(12) United States Patent
Kanios et al.

(10) Patent No.: US 8,591,941 B2
(45) Date of Patent: Nov. 26, 2013

(54) TRANSDERMAL DRUG DELIVERY DEVICE INCLUDING AN OCCLUSIVE BACKING

(75) Inventors: David Kanios, Miami, FL (US); Juan A. Mantelle, Miami, FL (US); Viet Nguyen, Miami, FL (US)

(73) Assignee: Noven Pharmaceuticals, Inc., Miami, FL (US)

( * ) Notice: Subject to any disclaimer, the term of this patent is extended or adjusted under 35 U.S.C. 154(b) by 0 days.

(21) Appl. No.: 13/198,405

(22) Filed: Aug. 4, 2011

(65) Prior Publication Data

US 2012/0165762 A1 Jun. 28, 2012

Related U.S. Application Data

(63) Continuation of application No. 11/245,180, filed on Oct. 7, 2005, now abandoned.

(60) Provisional application No. 60/616,861, filed on Oct. 8, 2004.

(51) Int. Cl.
*A61K 9/70* (2006.01)

(52) U.S. Cl.
USPC .......................................................... 424/449

(58) Field of Classification Search
None
See application file for complete search history.

(56) References Cited

U.S. PATENT DOCUMENTS

| | | |
|---|---|---|
| 4,390,520 A | 6/1983 | Nagai et al. |
| 4,559,222 A | 12/1985 | Enscore et al. |
| 4,584,355 A | 4/1986 | Blizzard et al. |
| 4,585,836 A | 4/1986 | Homan et al. |
| 4,591,622 A | 5/1986 | Blizzard et al. |
| 4,655,767 A | 4/1987 | Woodard et al. |
| 4,994,278 A | 2/1991 | Sablotsky et al. |
| 5,246,705 A | 9/1993 | Venkatraman et al. |
| 5,446,070 A | 8/1995 | Mantelle |
| 5,474,783 A | 12/1995 | Miranda et al. |
| 5,474,787 A | 12/1995 | Grey et al. |
| 5,656,286 A | 8/1997 | Miranda et al. |
| 5,762,952 A | 6/1998 | Barnhart et al. |
| 5,958,446 A | 9/1999 | Miranda et al. |
| 6,024,976 A | 2/2000 | Miranda et al. |
| 6,221,383 B1 | 4/2001 | Miranda et al. |
| 6,235,306 B1 | 5/2001 | Miranda et al. |
| 6,562,363 B1 | 5/2003 | Mantelle et al. |

(Continued)

FOREIGN PATENT DOCUMENTS

| | | |
|---|---|---|
| WO | WO 97/23205 A1 | 7/1997 |
| WO | WO 02/36103 A1 | 5/2002 |
| WO | WO 2005/046600 A2 | 5/2005 |
| WO | WO 2006/028863 A1 | 3/2006 |

OTHER PUBLICATIONS

Supplementary Partial European Search Report issued on Nov. 19, 2009 in application No. EP 05815555.

(Continued)

*Primary Examiner* — Anand Desai
*Assistant Examiner* — Melissa Mercier
(74) *Attorney, Agent, or Firm* — Foley & Lardner LLP

(57) ABSTRACT

A transdermal drug delivery system for the topical application of one or more active agents contained in one or more polymeric and/or adhesive carrier layers, proximate to a non-drug containing polymeric backing layer which can control the delivery rate and profile of the transdermal drug delivery system by adjusting the moisture vapor transmission rate of the polymeric backing layer.

15 Claims, 2 Drawing Sheets

(56) References Cited

U.S. PATENT DOCUMENTS

| | | |
|---|---|---|
| 2001/0051180 A1 | 12/2001 | Watanabe et al. |
| 2002/0128345 A1 | 9/2002 | Paul |
| 2003/0170195 A1* | 9/2003 | Houze et al. .............. 424/70.16 |
| 2006/0034905 A1 | 2/2006 | Singh et al. |
| 2006/0078604 A1 | 4/2006 | Kanios et al. |

OTHER PUBLICATIONS

Vaughan, "Using Solubility Parameters in Cosmetics Formulation," J. Soc. Cosmet. Chem., vol. 36, pp. 319-333, 1985.

Sobieski et al., "Silicone Pressure Sensitive Adhesives," Handbook of Pressure-Sensitive Adhesive Technology, $2^{nd}$ ed., pp. 508-517, 1989.

Zettl, "Acrylic Adhesives," Handbook of Pressure-Sensitive Adhesive Technology, $2^{nd}$ ed., pp. 396-456, 1989.

Merck Index, $11^{th}$ ed., Merck & Co., Rahway, NJ, pp. ther-5 to ther-29, 1980.

Nemec et al., "Acrylic and Methacrylic Acid Polymers," Polymer Science and Engineering, vol. 1, $2^{nd}$ ed., pp. 234-268, 1984.

International Search Report issued in application No. PCT/US05/35806 on May 2, 2006).

Office Action issued Aug. 13, 2009 by the Examiner in U.S. Appl. No. 11/245,180 (US 2006/0078604).

Office Action issued Oct. 27, 2009 by the Examiner in U.S. Appl. No. 11/245,180 (US 2006/0078604).

Office Action issued Jul. 12, 2010 by the Examiner in U.S. Appl. No. 11/245,180 (US 2006/0078604).

\* cited by examiner

TRANSDERMAL DRUG DELIVERY DEVICE INCLUDING AN OCCLUSIVE BACKING

This application claims the benefit of provisional application 60/616,861 filed Oct. 8, 2004, which is hereby incorporated by reference in its entirety.

FIELD OF THE INVENTION

This invention relates generally to transdermal drug delivery systems, and more particularly to pharmaceutically acceptable adhesive matrix compositions. The invention additionally relates to transdermal drug delivery systems providing acceptable drug release profiles for an extended period of time of up to seven days or longer.

In particular, the present invention is directed to a transdermal drug delivery system for the topical application of one or more active agents contained in one or more polymeric and/or adhesive carrier layers, proximate to a non-drug containing polymeric backing layer. The backing layer can be processed or manufactured separately from the polymeric and/or adhesive drug carrier layer(s) to prevent or minimize loss of drug or other system components, and combined prior to topical application. In the alternative, the backing device can be processed together with the polymeric and/or adhesive drug carrier layer(s). The drug delivery rate and profile can be controlled by adjusting certain characteristics of the polymeric backing layer.

BACKGROUND OF THE INVENTION

The use of transdermal drug delivery systems to topically administer an active agent is well known. These systems incorporate the active agent into a carrier composition, such as a polymeric and/or pressure-sensitive adhesive composition, from which the active agent is delivered through the skin or mucosa of the user.

Many factors influence the design and performance of such drug delivery devices, such as the individual drugs themselves, the physical/chemical characteristics of the system's components and the performance/behavior relative to other system components once combined, external/environmental conditions during manufacturing and storage thereafter, the properties of the topical site of application, the desired rate of drug delivery and onset, the drug delivery profile, and the intended duration of delivery. Cost, appearance, size and ease of manufacturing are also important considerations.

Active-ingredient-containing transdermal drug delivery systems ("patches") are essentially divided into two major technical systems: reservoir systems and matrix systems. The present invention relates to matrix systems where the active ingredient(s) are embedded in a semi-solid matrix made up of a single polymer or a blend of polymers.

Both types of devices employ a backing layer that forms the protective outer surface of the finished transdermal system and which is exposed to the environment during use. A release liner or protective layer that forms the inner surface covers the polymeric adhesive which is employed for affixing the system to the skin or mucosa of a user. The release liner or protective layer is removed prior to application, exposing the adhesive, typically a pressure-sensitive adhesive.

In the "classic" reservoir-type device, the active agent is typically dissolved or dispersed in a carrier to yield a non-finite carrier form, such as, for example, a fluid or gel. In the reservoir-type device, the active agent is generally kept separate from the adhesive. The device has a pocket or "reservoir" which physically serves to hold the active agent and carrier, and which is formed in or by a backing layer. A peripheral adhesive layer is then used to affix the device to the user.

The reservoir-type devices have a number of disadvantages including a non-uniform drug release profile where a high dose of drug is initially released upon application to the user, often described as a "burst effect." This burst or high initial release of drug then drops off after a period of time to a rate that necessary to achieve a therapeutically effective amount. Drug delivery according to this profile is generally described as first order release.

While classic reservoir-type devices are still in use today, the term reservoir is being used interchangeably herein with matrix-type devices which still rely upon a separate adhesive means used to affix the device to the user.

In a matrix-type device, the active agent is dissolved or dispersed in a carrier that typically is in a finite carrier form. The carrier form can be self-adhesive or non-adhesive. Non-adhesive matrix-type devices, that is, those which still rely on a separate adhesive means to affix the device to the user, employ a drug permeable adhesive layer (often referred to as an "in-line adhesive" since the drug must pass through this layer) applied over the drug matrix carrier layer. To better control the release rate of the drug, the non-adhesive matrix-type devices often employ one or more additional drug permeable layers such as, for example, rate controlling membranes. The non-adhesive matrix-type devices often contain excipients, such as drug delivery enhancers, to help control the release rate. These devices are often referred to as multi-layer or multilaminate.

In a "monolithic" or "monolayer" matrix-type device, the active agent is typically solubilized or homogenously blended in an adhesive carrier composition, typically a pressure-sensitive adhesive or bioadhesive, which functions as both the drug carrier and the means of affixing the system to the skin or mucosa. Such devices, commonly referred to as drug-in-adhesive devices, are described, for example, in U.S. Pat. Nos. 4,994,267; 5,446,070; 5,474,783 and 5,656,286, all of which are assigned to Noven Pharmaceuticals, Inc., Miami, Fla. and herein incorporated by reference.

While matrix-type devices, especially drug-in-adhesive devices, achieve more uniform and controlled drug deliver rates over longer periods of time, most transdermal systems remain subject to a higher initial drug release than is required to achieve therapeutic efficacy. For many drugs and/or therapeutic situations, it would be advantageous to eliminate or suppress this higher initial release and achieve a "steady state" (zero order) release profile which uniformly delivers a therapeutically effective amount of drug over the extended duration of device's desired use, preferably up to 7 days or more.

The high initial blood level concentration of certain drugs may cause adverse or undesired effects, or create toxicity concerns, thereby limiting the use of transdermal administration. In other instances, the higher initial blood level concentration may reduce the amount of drug required for treatment to the point of risking under dosing, or the higher initial blood level concentration may make it impractical to increase the duration of the device's application while retaining therapeutic effectiveness. Reducing the frequency of replacing the transdermal drug delivery system would increase user compliance, reduce any lag or drop off in efficacious blood levels, and reduce the amount of drug required for treatment (also provided by reducing the higher initial blood level associated with the higher release rate).

Drug concentration in transdermal delivery systems can vary widely depending on the drug and polymers used. Low drug concentrations in the adhesive can result in difficulties in achieving an acceptable delivery rate of the medicament, preferably one approximating zero order kinetics. High drug concentrations, on the other hand, frequently affect the adhesion properties of the adhesives, and tend to promote unwanted crystallization.

Simple diffusion models for permeation of drugs through the skin suggest that permeation rates are concentration dependent, that is, dependent on both the amount and the degree of drug within the pressure-sensitive adhesive composition. Some adhesives, such as, for example, polyacrylate adhesives have a high affinity for many drugs and thus tend to solubilize higher concentrations of drug than do, for example, rubber adhesives. However, the use of polyacylates alone as the adhesive is not without its drawbacks as polyacrylate adhesives, for example, may tend to cause skin irritation, especially when the transdermal device is used for extended periods of time.

Various transdermal drug delivery systems have been described in the literature. For example, U.S. Pat. No. 4,559,222 describes a multi-layer non-adhesive matrix-type device having a reservoir layer which comprises mineral oil, colloidal silicon dioxide, a polyisobutylene adhesive and a drug, which may be clonidine, at a concentration greater than saturation. The system includes a drug release rate controlling layer through which the drug may diffuse at a known rate, an adhesive layer, which may also contain a loading of drug, and a protective strippable coating.

U.S. Pat. No. 5,762,952 describes a system comprising a self-crosslinking acrylate adhesive into which a drug, such as clonidine, is incorporated together with auxiliaries, such as solvents or absorption promoters, that are volatile at relatively high temperatures. The patent discusses that the crosslinked acrylate adhesive is important to increase the consistency of the adhesive substance and to incorporate either a large amount of the active drug or a large amount of an inactive solubilizin Thus, it would therefore be desirable to provide a system for use with many types of drugs, in which the permeation rate and profile can be easily adjusted by employing a backing layer to modulate flux of drug through the skin or mucosa and while providing an active agent-containing carrier composition formulated in a simple and cost effective manner. It would be further advantageous to avoid drug loss encountered in manufacturing methods requiring high temperature heating or drying after addition of a drug to the carrier composition.

SUMMARY OF THE INVENTION

Based upon the foregoing, it is an object of the present invention to overcome the limitations of the prior transdermal systems, and to provide a transdermal drug delivery system which allows selective modulation of drug permeation and delivery rates and profiles.

Another object is to provide a transdermal system, which is simple and inexpensive to manufacture. The present invention provides a transdermal drug delivery system for the topical application of one or more active agents contained in one or more polymeric and/or adhesive carrier layers, proximate to a non-drug containing polymeric backing layer which is manufactured to optimize drug loading while providing desirable adhesion to skin or mucosa as well as providing modulation of the drug delivery and profile. The polymeric backing layer is designed to provide control of permeation rate, onset and profile of the active agent from the system.

The transdermal delivery device may comprise at least one layer formed of a single polymer or a blend of polymers to serve as a pressure-sensitive adhesive composition for applying the system to the dermis.

The invention is also directed to compositions and methods of controlling drug delivery rates, onset and profiles of at least one active agent in a transdermal delivery system, comprising selecting a specific a non-drug containing polymeric backing layer having specific physical and/or chemical characteristics. The drug carrier composition may be comprised of (a) one or more acrylic-based polymers having one or more functionality or (b) one or more silicone-based polymers having one or more silanol contents (capping) and/or resin to polymer ratios, alone or in combination, and are present in proportions to provide a desired solubility for the drug. By selectively tailoring the moisture vapor transmission rate of the backing layer, drug delivery, onset and profiles can be achieved.

For a better understanding of the present invention, together with other and further objects thereof, reference is made to the following description, taken in conjunction with the accompanying drawings, and its scope will be pointed out in the appending claims. Further embodiments of the invention include those described in the detailed description.

DETAILED DESCRIPTION OF THE PREFERRED EMBODIMENTS

Figure 1:
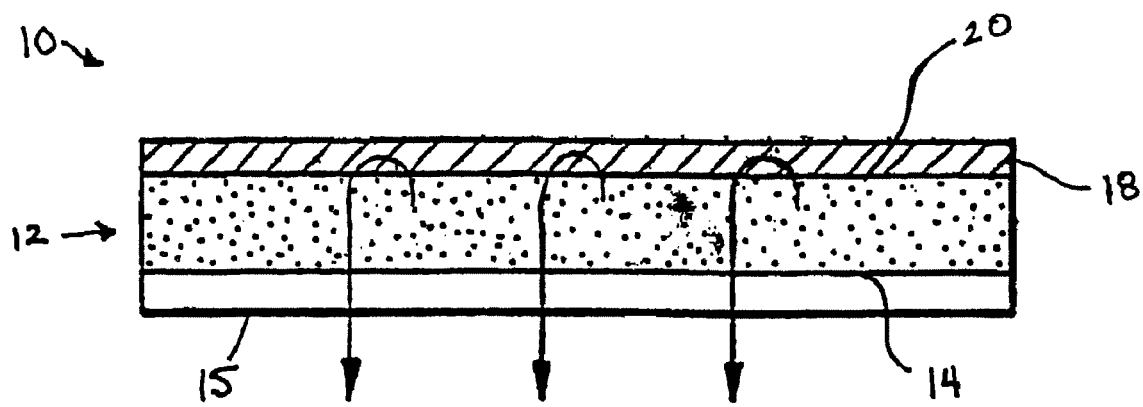
FIG. 1 shows a schematic cross-sectional view of a transdermal delivery device according to an embodiment of the invention prior to use.

The foregoing and other objects are achieved by this invention which provides a transdermal drug delivery system to provide an adhesive matrix composition which effectively delivers drugs to a user over an extended period of time.

Unless defined otherwise, all technical and scientific terms used herein have the same meaning as commonly understood by one of ordinary skill in the art to which the invention pertains.

As used herein, the term "pressure-sensitive adhesive" refers to a viscoelastic material which adheres almost instantaneously to most substrates with the application of very slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizers or other additives. The term pressure-sensitive adhesive also includes mixtures of different polymers and mixtures of polymers, such as polyisobutylenes (PIB) of different molecular weights, the resultant mixtures being a pressure-sensitive adhesive. In the last case, the polymers of lower molecular weight in the mixture are not considered to be "tackifiers," the term "tackifier" being reserved for additives which differ other than in molecular weight from the polymers to which they are added.

The term "topical" or "topically" is used herein in its conventional meaning as referring to direct contact with an anatomical site or surface area on a mammal including skin, teeth, nails and mucosa.

The term "mucosa" as used herein means any moist anatomical membrane or surface on a mammal such as oral, buccal, vaginal, rectal, nasal or ophthalmic surfaces.

The term "transdermal" as used herein means passage into and/or through skin or mucosa for localized or systemic delivery of an active agent.

As used herein, the terms "blend" and "mixture" are used herein to mean that there is no, or substantially no, chemical reaction or crosslinking (other than simple H-bonding) between the different polymers in the polymer matrix. However, crosslinking between a single polymer component is fully contemplated to be within the scope of the present invention.

The term "adhesive" means a substance, inorganic or organic, natural or synthetic that is capable of surface attachment at the intended topical application site by itself or functions as an adhesive by admixture with tackifiers, plasticizers, cross-linking agents or other additives.

In the most preferred embodiment, the carrier of the present invention is a "pressure-sensitive adhesive" which refers to a viscoelastic material which adheres instantaneously to most substrates with the application of very slight pressure and remains permanently tacky. A polymer or dermal composition is a pressure-sensitive adhesive within the meaning of the term as used herein if it has the adhesive properties of a pressure-sensitive adhesive per se or functions as a pressure-sensitive adhesive by admixture with tackifiers, plasticizers, cross-linking agents or other additives.

As used herein, a "polymer composition of two or more polymers" is defined as a physical blend of at least two polymers and can include 3 or more polymers. The two or more polymers may include the acrylic-based polymers described herein and can optionally include other polymers discussed more fully below.

The term "acrylic-based" polymer is defined as any polyacrylate, polyacrylic, acrylate and acrylic polymer. The acrylic-based polymers can be any of the homopolymers, copolymers, terpolymers, and the like of various acrylic acids or esters. The acrylic-based polymers useful in practicing the invention are polymers of one or more monomers of acrylic acids and other copolymerizable monomers. The acrylic-based polymers also include copolymers of alkyl acrylates and/or methacrylates and/or copolymerizable secondary monomers. Acrylic-based polymers with functional groups as described more fully below, are copolymerized with functional monomers.

As used herein, "functionality" is broadly defined as a measure of the type and quantity of functional groups that a particular acrylic-based polymer has.

As used herein, "functional monomers or groups," are monomer units in acrylic-based polymers which have reactive chemical groups which modify the acrylic-based polymers directly or provide sites for further reactions. Examples of functional groups include carboxyl, epoxy and hydroxy groups.

As used herein "non-functional acrylic-based polymer" is defined as an acrylic-based polymer that has no or substantially no functional reactive moieties present in the acrylic. These are generally acrylic esters which can be copolymerized with other monomers which do not have functional groups, such as vinyl acetate.

The term "carrier" as used herein refers to any non-aqueous material known in the art as suitable for transdermal drug delivery administration, and includes any polymeric material into which an active agent may be solubilized in combination or admixture with the other ingredients of the composition. The polymeric materials preferably comprise adhesives and, in particular, pressure-sensitive adhesives. The carrier material is typically used in an amount of about 40% to about 90%, and preferably from about 50% to about 80%, by weight based on the dry weight of the total carrier composition.

The term "carrier composition" may also refer to enhancers, solvents, co-solvents and other types of addictives useful for facilitating transdermal drug delivery.

The carrier compositions of the present invention can also contain one or more non-aqueous solvents and/or co-solvents. Such solvents and/or co-solvents are those known in the art, and are non-toxic, pharmaceutically acceptable substances, preferably non-aqueous liquids, which do not substantially negatively affect the adhesive properties or the solubility of the active agents at the concentrations used. The solvent and/or co-solvent can be for the active agent or for the carrier materials, or both.

Suitable solvents include volatile processing liquids such as alcohols (e.g., methyl, ethyl, isopropyl alcohols and methylene chloride); ketones (e.g., acetone); aromatic hydrocarbons such as benzene derivatives (e.g., xylenes and toluenes); lower molecular weight alkanes and cycloalkanes (e.g., hexanes, heptanes and cyclohexanes); and alkanoic acid esters (e.g., ethyl acetate, n-propyl acetate, isobutyl acetate, n-butyl acetate isobutyl isobutyrate, hexyl acetate, 2-ethylhexyl acetate or butyl acetate); and combinations and mixtures thereof. Other suitable co-solvents include polyhydric alcohols, which include glycols, triols and polyols such as ethylene glycol, diethylene glycol, propylene glycol, dipropylene glycol, trimethylene glycol, butylene glycol, polyethylene glycol, hexylene glycol, polyoxyethylene, glycerin, trimethylpropane, sorbitol, polyvinylpyrrolidone, and the like. Alternatively, co-solvents may include glycol ethers such as ethylene glycol monoethyl ether, glycol esters, glycol ether esters such as ethylene glycol monoethyl ether acetate and ethylene glycol diacetate; saturated and unsaturated fatty acids, mineral oil, silicone fluid, lecithin, retinol derivatives and the like, and ethers, esters and alcohols of fatty acids. As will be described in more detail hereafter, the solvents or co-solvents used in accordance with the invention are desirably a low volatile solvent that does not require excessive temperatures for evaporation thereof.

The term "solubilized" is intended to mean that in the carrier composition there is an intimate dispersion or dissolution of the active agent at the crystalline, molecular or ionic level, such that crystals of the active agent cannot be detected using a microscope having a magnification of 25×. As such, the active agent is considered herein to be in "non-crystallized" form when in the compositions of the present invention.

As used herein "flux" is defined as the percutaneous absorption of drugs through the skin, and is described by Fick's first law of diffusion:

$$J = -D(dC_m/dx),$$

where J is the flux in g/cm$^2$/sec, D is the diffusion coefficient of the drug through the skin in cm$^2$/sec and $dC_m/dx$ is the concentration gradient of the active agent across the skin or mucosa.

As used herein, "therapeutically effective" means an amount of an active agent that is sufficient to achieve the desired local or systemic effect or result, such as to prevent, cure, diagnose, mitigate or treat a disease or condition, when applied topically over the duration of intended use. The amounts necessary are known in the literature or may be determined by methods known in the art, but typically range from about 0.1 mg to about 20,000 mg, and preferably from about 0.1 mg to about 1,000 mg, and most preferably from about 0.1 to about 500 mg per human adult or mammal of about 75 kg body weight per 24 hours.

The term "about", and the use of ranges in general whether or not qualified by the term about, means that the number comprehended is not limited to the exact number set forth herein, and is intended to refer to ranges substantially within the quoted range not departing from the scope of the invention.

The term "user" or "subject" is intended to include all warm-blooded mammals, preferably humans.

The phrase "substantially zero-order" as used herein means transdermal delivery of an active agent at a release rate which is approximately constant once steady state is attained, typically within 12 to 24 hours after topical application. While variability in blood levels of active agent are contemplated within the scope of this meaning once steady state release is attained, the depletion rate of active agent over the duration of use should typically not exceed about 20% to about 25%.

As used herein, the term "rubber" refers to a viscoelastic material which has the properties of a pressure-sensitive adhesive and which contains at least one natural or synthetic elastomeric polymer. Suitable rubbers include polysiloxane, polyisobutylene and natural rubber.

Solubility parameter, also referred to herein as "SP," has been defined as the sum of all the intermolecular attractive forces, which are empirically related to the extent of mutual solubility of many chemical species. A general discussion of solubility parameters is found in an article by Vaughan, "Using Solubility Parameters in Cosmetics Formulation," *J. Soc. Cosmet. Chem.*, Vol. 36, pages 319-333 (1985).

The multiple polymer adhesive system is preferably formulated so that it is a pressure-sensitive adhesive at room temperature and has other desirable characteristics for adhesives used in the transdermal drug delivery art. Such characteristics include good adherence to skin, ability to be peeled or otherwise removed without substantial trauma to the skin, retention of tack with aging, etc. In general, the multiple polymer adhesive system should have a glass transition temperature (Tg), measured using a differential scanning calorimeter, of between about −70° C. and 0° C.

Further details and examples of silicone pressure-sensitive adhesives which are useful in the practice of this invention are described in the following U.S. Pat. Nos. 4,591,622; 4,584,355; 4,585,836; and 4,655,767. These patents are incorporated herein by reference.

The term "active agent" (and its equivalents "agent," "drug," "medicament" and "pharmaceutical") is intended to have the broadest meaning and includes at least one of any therapeutic, prophylactic, pharmacological or physiological active substance, cosmetic and personal care preparations, and mixtures thereof, which is delivered to a mammal to produce a desired, usually beneficial, effect. More specifically, any active agent that is capable of producing a pharmacological response, localized or systemic, irrespective of whether therapeutic, diagnostic, cosmetic or prophylactic in nature, is within the contemplation of the invention. Also within the invention are such bioactive agents as pesticides, insect repellents, sun screens, cosmetic agents, etc. It should be noted that the drugs and/or bioactive agents may be used singularly or as a mixture of two or more such agents, and in amounts sufficient to prevent, cure, diagnose or treat a disease or other condition, as the case may be. The drugs and mixtures thereof can be present in the composition in different forms, depending on which form yields the optimum delivery characteristics. Thus, in the case of drugs, the drug can be in its free base or acid form, or in the form of salts, esters, amides, prodrugs, enantiomers or mixtures thereof, or any other pharmacologically acceptable derivatives, or as components of molecular complexes.

The drug is used in a "pharmacologically effective amount." This term means that the concentration of the drug is such that in the composition it results in a therapeutic level of drug delivered over the term that the transdermal dosage form is to be used, preferably with zero order kinetics. Such delivery is dependent on a great number of variables including the drug, the time period for which the individual dosage unit is to be used, the flux rate of the drug from the system and a number of other variables. The amount of drug needed can be experimentally determined based on the flux rate of the drug through the system and through the skin when used with and without enhancers. Having determined the flux rate needed, the transdermal delivery system is designed so that the release rate over the period of time of therapeutic use will be at least equal to the flux rate. Of course, the surface area of the transdermal delivery system also affects the delivery of the drug from the system.

Drugs in general can be used in this invention. These drugs include those categories and species of drugs set forth on page they-5 to ther-29 of the *Merck Index,* 11th Edition Merck & Co. Rahway, N.J. (1989).

1. α-Adrenergic agonists such as Adrafinil, Adrenolone, Amidephrine, Apraclonidine, Budralazine, Clonidine, Cyclopentamine, Detomidine, Dimetofrine, Dipivefrin, Ephedrine, Epinephrine, Fenoxazoline, Guanabenz, Guanfacine, Hydroxyamphetamine, Ibopamine, Indanazoline, Isometheptene, Mephentermine, Metaraminol, Methoxamine Hydrochloride, Methylhexaneamine, Metizolene, Midodrine, Naphazoline, Norepinephrine, Norfenefrine, Octodrine, Octopamine, Oxymetazoline, Phenylephrine Hydrochloride, Phenylpropanolamine Hydrochloride, Phenylpropylmethylamine, Pholedrine, Propylhexedrine, Pseudoephedrine, Rilmenidine, Synephrine, Tetrahydrozoline, Tiamenidine, Tramazoline, Tuaminoheptane, Tymazoline, Tyramine and Xylometazoline.

2. β-Adrenergic agonists such as Albuterol, Bambuterol, Bitolterol, Carbuterol, Clenbuterol, Clorprenaline, Denopamine, Dioxethedrine, Dopexamine, Ephedrine, Epinephrine, Etafedrine, Ethylnorepinephrine, Fenoterol, Formoterol, Hexoprenaline, Ibopamine, Isoetharine, Isoproterenal, Mabuterol, Metaproterenol, Methoxyphenamine, Oxyfedrine, Pirbuterol, Prenalterol, Procaterol, Protokylol, Reproterol, Rimiterol, Ritodrine, Soterenol, Terbuterol and Xamoterol.

3. α-Adrenergic blockers such as Amosulalol, Arotinolol, Dapiprazole, Doxazosin, Ergoloid Mesylates, Fenspiride, Indoramin, Labetalol, Nicergoline, Prazosin, Terazosin, Tolazoline, Trimazosin and Yohimbine.

4. β-Adrenergic blockers such as Acebutolol, Alprenolol, Amosulalol, Arotinolol, Atenolol, Befunolol, Betaxolol, Bevantolol, Bisoprolol, Bopindolol, Bucumolol, Befetolol, Bufuralol, Bunitrolol, Bupranolol, Butidrine Hydrochloride, Butofilolol, Carazolol, Carteolol, Carvedilol, Celiprolol, Cetamolol, Cloranolol, Dilevalol, Epanolol, Esmolol, Indenolol, Labetalol, Levobunolol, Mepindolol, Metipranalol, Metoprolol, Moprolol, Nadoxolol, Nifenalol, Nipradilol, Oxprenolol, Penbutolol, Pindolol, Practolol, Pronethalol, Propranolol, Sotalol, Sulfinalol, Talinolol, Tertatolol, Timolol, Toliprolol and Xibenolol.

5. Alcohol deterrents such as Calcium Cyanamide Citrated, Disulfuram, Nadide and Nitrefazole.

6. Aldose reductase inhibitors such as Epalrestat, Ponalrestat, Sorbinil and Tolrestat.

7. Anabolics such as Androisoxazole, Androstenediol, Bolandiol, Bolasterone, Clostebol, Ethylestrenol, Formyldienolone, 4-Hydroxy-19-nortestosterone, Methandriol, Methenolone, Methyltrienolone, Nandrolone, Nandrolone Decanoate, Nandrolone p-Hexyloxyphenylpropionate, Nandrolone Phenpropionate, Norbolethone, Oxymesterone, Pizotyline, Quinbolone, Stenbolone and Trenbolone.

8. Analgesics (dental) such as Chlorobutanol, Clove and Eugenol.

9. Analgesics (narcotic) such as Alfentanil, Allylprodine, Alphaprodine, Anileridine, Benzylmorphine, Bezitramide, Buprenorphine, Butorphanol, Clonitazene, Codeine, Codeine Methyl Bromide, Codeine Phosphate, Codeine Sulfate, Desomorphine, Dextromoramide, Dezocine, Diampromide, Dihydrocodeine, Dihydrocodeinone Enol Acetate, Dihydromorphine, Dimenoxadol, Dimepheptanol, Dimethylthiambutene, Dioxaphetyl Butyrate, Dipipanone, Eptazocine, Ethoheptazine, Ethylmethylthiambutene, Ethylmorphine, Etonitazene, Fentanyl, Hydrocodone, Hydrocodone Bitartrate, Hydromorphone, Hydroxypethidine, Isomethadone, Ketobemidone, Levorphanol, Lofentanil, Meperidine, Meptazinol, Metazocine, Methadone Hydrochloride, Metopon, Morphine, Morphine Derivatives, Myrophine, Nalbuphine, Narceine, Nicomorphine, Norlevorphanol, Normethadone, Normorphine, Norpipanone, Opium, Oxycodone, Oxymorphone, Papavereturn, Pentazocine, Phenadoxone, Phenazocine, Pheoperidine, Piminodine, Piritramide, Proheptazine, Promedol, Properidine, Propiram, Propoxyphene, Sufentanil and Tilidine.

10. Analgesics (non-narcotic) such as Acetaminophen, Acetaminosalol, Acetanilide, Acetylsalicylsalicylic Acid, Alclofenac, Alminoprofen, Aloxiprin, Aluminum Bis(acetylsalicylate), Aminochlorthenoxazin, 2-Amino-4-picoline, Aminopropylon, Aminopyrine, Ammonium Salicylate, Antipyrine, Antipyrine Salicylate, Antrafenine, Apazone, Aspirin, Benorylate, Benoxaprofen, Benzpiperylon, Benzydamine, p-Bromoacetanilide, 5-Bromosalicylic Acid Acetate, Bucetin, Bufexamac, Bumadizon, Butacetin, Calcium Acetylsalicylate, Carbamazepine, Carbetidine, Carbiphene, Carsalam, Chloralantipyrine, Chlorthenoxazin(e), Choline Salicylate, Cinchophen, Ciramadol, Clometacin, Cropropamide, Crotethamide, Dexoxadrol, Difenamizole, Diflunisal, Dihydroxyaluminum Acetylsalicylate, Dipyrocetyl, Dipyrone, Emorfazone, Enfenamic Acid, Epirizole, Etersalate, Ethenzamide, Ethoxazene, Etodolac, Felbinac, Fenoprofen, Floctafenine, Flufenamic Acid, Fluoresone, Flupirtine, Fluproquazone, Flurbiprofen, Fosfosal, Gentisic Acid, Glafenine, Ibufenac, Imidazole Salicylate, Indomethacin, Indoprofen, Isofezolac, Isoladol, Isonixin, Ketoprofen, Ketorolac, p-Lactophenetide, Lefetamine, Loxoprofen, Lysine Acetylsalicylate, Magnesium Acetylsalicylate, Methotrimeprazine, Metofoline, Miroprofen, Morazone, Morpholine Salicylate, Naproxen, Nefopam, Nifenazone, 5' Nitro-2' propoxyacetanilide, Parsalmide, Perisoxal, Phenacetin, Phenazopyridine Hydrochloride, Phenocoll, Phenopyrazone, Phenyl Acetylsalicylate, Phenyl Salicylate, Phenyramidol, Pipebuzone, Piperylone, Prodilidine, Propacetamol, Propyphenazone, Proxazole, Quinine Salicylate, Ramifenazone, Rimazolium Metilsulfate, Salacetamide, Salicin, Salicylamide, Salicylamide O-Acetic Acid, Salicylsulfuric Acid, Salsalte, Salverine, Simetride, Sodium Salicylate, Sulfamipyrine, Suprofen, Talniflumate, Tenoxicam, Terofenamate, Tetradrine, Tinoridine, Tolfenamic Acid, Tolpronine, Tramadol, Viminol, Xenbucin and Zomepirac.

11. Anesthetics such as Acetamidoeugenol, Alfadolone Acetate, Alfaxalone, Amucaine, Amolanone, Amylocalne Hydrochloride, Benoxinate, Benzocaine, Betoxycaine, Biphenamine, Bupivacaine, Butacaine, Butaben, Butanilicaine, Burethamine, Buthalital Sodium, Butoxycaine, Carticaine, 2-Chloroprocaine Hydrochloride, Cocaethylene, Cocaine, Cyclomethycaine, Dibucaine Hydrochloride, Dimethisoquin, Dimethocaine, Diperadon Hydrochloride, Dyclonine, Ecgonidine, Ecgonine, Ethyl Aminobenzoate, Ethyl Chloride, Etidocaine, Etoxadrol, β-Eucaine, Euprocin, Fenalcomine, Fomocaine, Hexobarbital, Hexylcaine Hydrochloride, Hydroxydione Sodium, Hydroxyprocaine, Hydroxytetracaine, Isobutyl p-Aminobenzoate, Kentamine, Leucinocaine Mesylate, Levoxadrol, Lidocaine, Mepivacaine, Meprylcaine Hydrochloride, Metabutoxycaine Hydrochloride, Methohexital Sodium, Methyl Chloride, Midazolam, Myrtecaine, Naepaine, Octacaine, Orthocaine, Oxethazaine, Parethoxycaine, Phenacaine Hydrochloride, Phencyclidine, Phenol, Piperocaine, Piridocaine, Polidocanol, Pramoxine, Prilocalne, Procaine, Propanidid, Propanocaine, Proparacaine, Propipocaine, Propofol, Propoxycaine Hydrochloride, Pseudococaine, Pyrrocaine, Quinine Urea Hydrochloride, Risocaine, Salicyl Alcohol, Tetracaine Hydrochloride, Thialbarbital, Thimylal, Thiobutabarbital, Thiopental Sodium, Tolycaine, Trimecaine and Zolamine.

12. Anorexics such as Aminorex, Amphecloral, Amphetamine, Benzaphetamine, Chlorphentermine, Clobenzorex, Cloforex, Clortermine, Cyclexedrine, Destroamphetamine Sulfate, Diethylpropion, Diphemethoxidine, N-Ethylamphetamine, Fenbutrazate, Fenfluramine, Fenproporex, Furfurylmethylamphetamine, Levophacetoperate, Mazindol, Mefenorex, Metamfeproamone, Methamphetamine, Norpseudoephedrine, Phendimetrazine, Phendimetrazine Tartrate, Phenmetrazine, Phenpentermine, Phenylpropanolamine Hydrochloride and Picilorex.

13. Anthelmintics (Cestodes) such as Arecoline, Aspidin, Aspidinol, Dichlorophen(e), Embelin, Kosin, Napthalene, Niclosamide, Pellertierine, Pellertierine Tannate and Quinacrine.

14. Anthelmintics (Nematodes) such as Alantolactone, Amoscanate, Ascaridole, Bephenium, Bitoscanate, Carbon Tetrachloride, Carvacrol, Cyclobendazole, Diethylcarbamazine, Diphenane, Dithiazanine Iodide, Dymanthine, Gentian Violet, 4-Hexylresorcinol, Kainic Acid, Mebendazole, 2-Napthol, Oxantel, Papain, piperazine, piperazine Adipate, piperazine Citrate, piperazine Edetate Calcium, piperazine Tartrate, Pyrantel, Pyrvinium Pamoate, a-Santonin, Stilbazium Iodide, Tetrachloroethylene, Tetramisole, thiabendazole, Thymol, Thymyl N-Isoamylcarbamate, Triclofenol piperazine and Urea Stibamine.

15. Anthelmintics (Onchocerca) such as Ivermectin and Suramin Sodium.

16. Anthelmintics (Schistosoma) such as Amoscanate, Amphotalide, Antimony Potassium Tartrate, Antimony Sodium Gluconate, Antimony Sodium Tartrate, Antimony Sodium Thioglycollate, Antimony Thioglycollamide, Becanthone, Hycanthone, Lucanthone Hydrochloride, Niridazole, Oxamniquine, Praziquantel, Stibocaptate, Stibophen and Urea Stibamine.

17. Anthelmintic (Trematodes) such as Anthiolimine and Tetrachloroethylene.

18. Antiacne drugs such as Adapelene, Algestone Acetophenide, Azelaic Acid, Benzoyl Peroxide, Cyoctol, Cyproterone, Motretinide, Resorcinol, Retinoic Acid, Tetroquinone and Tretinonine.

19. Antiallergics such as Amlexanox, Astemizole, Azelastine, Cromolyn, Fenpiprane, Histamine, Ibudilast, Nedocromil, Oxatomide, Pentigetide, Poison Ivy Extract, Poison Oak Extract, Poison Sumac Extract, Repirinast, Tranilast, Traxanox and Urushiol.

20. Antiamebics such as Arsthinol, Bialamicol, Carbarsone, Cephaeline, Chlorbetamide, Chloroquine, Chlorphenoxamide, Chlortetracycline, Dehydroemetine, Dibromopropamidine, Diloxanide, Dephetarsone, Emetine, Fumagillin, Glaucarubin, Glycobiarsol, 8-Hydroxy-7-iodo-5-quinolinesulfonic Acid, Iodochlorhydroxyquin, Iodoquinol, Paromomycin, Phanquinone, Phearsone Sulfoxylate, Polybenzarsol, Propamidine, Quinfamide, Secnidazole, Sulfarside, Teclozan, Tetracycline, Thiocarbamizine, Thiocarbarsone and Tinidazole.

21. Antiandrogens such as Bifluranol, Cyoctol, Cyproterone, Delmadinone Acetate, Flutimide, Nilutamide and Oxendolone.

22. Antianginals such as Acebutolol, Alprenolol, Amiodarone, Amlodipine, Arotinolol, Atenolol, Bepridil, Bevantolol, Bucumolol, Bufetolol, Bufuralol, Bunitrolol, Bupranolol, Carozolol, Carteolol, Carvedilol, Celiprolol, Cinepazet Maleate, Diltiazem, Epanolol, Felodipine, Gallopamil, Imolamine, Indenolol, Isosorbide Dinitrate, Isradipine, Limaprost, Mepindolol, Metoprolol, Molsidomine, Nadolol, Nicardipine, Nifedipine, Nifenalol, Nilvadipine, Nipradilol, Nisoldipine, Nitroglycerin, Oxprenolol, Oxyfedrine, Ozagrel, Penbutolol, Pentaerythritol Tetranitrate, Pindolol, Pronethalol, Propranolol, Sotalol, Terodiline, Timolol, Toliprolol and Verapamil.

23. Antiarrhythmics such as Acebutol, Acecaine, Adenosine, Ajmaline, Alprenolol, Amiodarone, Amoproxan, Aprindine, Arotinolol, Atenolol, Bevantolol, Bretylium Tosylate, Bubumolol, Bufetolol, Bunaftine, Bunitrolol, Bupranolol, Butidrine Hydrochloride, Butobendine, Capobenic Acid, Carazolol, Carteolol, Cifenline, Cloranolol, Disopyramide, Encamide, Esmolol, Flecamide, Gallopamil, Hydroquinidine, Indecamide, Indenolol, Ipratropium Bromide, Lidocaine, Lorajmine, Lorcamide, Meobentine, Metipranolol, Mexiletine, Moricizine, Nadoxolol, Nifenalol, Oxprenolol, Penbutolol, Pindolol, Pirmenol, Practolol, Prajmaline, Procainamide Hydrochloride, Pronethalol, Propafenone, Propranolol, Pyrinoline, Quinidine Sulfate, Quinidine, Sotalol, Talinolol, Timolol, Tocamide, Verapamil, Viquidil and Xibenolol.

24. Antiarteriosclerotics such as Pyridinol Carbamate.

25. Antiarthritic/Antirheumatics such as Allocupreide Sodium, Auranofin, Aurothioglucose, Aurothioglycanide, Azathioprine, Calcium 3-Aurothio-2-propanol-1-sulfonate, Celecoxib, Chloroquine, Clobuzarit, Cuproxoline, Diacerein, Glucosamine, Gold Sodium Thiomalate, Gold Sodium Thiosulfate, Hydroxychloroquine, Kebuzone, Lobenzarit, Melittin, Methotrexate, Myoral and Penicillamine.

26. Antibacterial (antibiotic) drugs including:

Aminoglycosides such as Amikacin, Apramycin, Arbekacin, Bambermycins, Butirosin, Dibekacin, Dihdrostreptomycin, Fortimicin(s), Gentamicin, Ispamicin, Kanamycin, Micronomicin, Neomycin, Neomycin Undecylenate, Netilmicin, Paromomycin, Ribostamycin, Sisomicin, Spectinomycin, Streptomycin, Streptonicozid and Tobramycin;

Amphenicols such as Azidamfenicol, Chloramphenicol, Chloramphenicol Palmitate, Chloramphenicol Pantothenate, Florfenicol and Thiamphenicol;

Ansamycins such as Rifamide, Rifampin, Rifamycin and Rifaximin;

β-Lactams, including:

Carbapenems such as Imipenem;

Cephalosporins such as Cefactor, Cefadroxil, Cefamandole, Cefatrizine, Cefazedone, Cefazolin, Cefixime, Cefmenoxime, Cefodizime, Cefonicid, Cefoperazone, Ceforanide, Cefotaxime, Cefotiam, Cefpimizole, Cefpirimide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine and Pivcefalexin;

Cephamycins such as Cefbuperazone, Cefmetazole, Cefminox, Cefetan and Cefoxitin;

Monobactams such as Aztreonam, Carumonam and Tigemonam;

Oxacephems such as Flomoxef and Moxolactam;

Penicillins such as Amidinocillin, Amdinocillin Pivoxil, Amoxicillin, Ampicillan, Apalcillin, Aspoxicillin, Azidocillan, Azlocillan, Bacampicillin, Benzylpenicillinic Acid, Benzylpenicillin Sodium, Carbenicillin, Carfecillin Sodium, Carindacillin, Clometocillin, Cloxacillin, Cyclacillin, Dicloxacillin, Diphenicillin Sodium, Epicillin, Fenbenicillin, Floxicillin, Hetacillin, Lenampicillin, Metampicillin, Methicillin Sodium, Mezlocillin, Nafcillin Sodium, Oxacillin, Penamecillin, Penethamate Hydriodide, Penicillin G Benethamine, Penicillin G Benzathine, Penicillin G Benzhydrylamine, Penicillin G Calcium, Penicillin G Hydrabamine, Penicillin G Potassium, Penicillin G Procaine, Penicillen N, Penicillin O, Penicillin V, Penicillin V Benzathine, Penicillin V Hydrabamine, Penimepicycline, Phenethicillin Potassium, Piperacillin, Pivapicillin, Propicillin, Quinacillin, Sulbenicillin, Talampicillin, Temocillin and Ticarcillin;

Lincosamides such as Clindamycin and Lincomycin;

Macrolides such as Azithromycin, Carbomycin, Clarithromycin, Erythromycin, Erythromycin Acistrate, Erythromycin Estolate, Erythromycin Glucoheptonate, Erythromycin Lactobionate, Erythromycin Propionate, Erythromycin Stearate, Josamycin, Leucomycins, Midecamycins, Miokamycin, Oleandomycin, Primycin, Rokitamycin, Rosaramicin, Roxithromycin, Spiramycin and Troleandomycin;

Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin B-Methanesulfonic Acid, Pristinamycin, Ristocetin, Teicoplanin, Thiostrepton, Tuberactinomycin, Tyrocidine, Tyrothricin, Vancomycin, Viomycin, Viomycin Pantothenate, Virginiamycin and Zinc Bacitracin;

Tetracyclines such as Apicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Senociclin and Tetracycline; and other antibiotics such as Cycloserine, Mupirocin and Tuberin.

27. Antibacterial drugs (synthetic), including:

2,4-Diaminopyrimidines such as Brodimoprim, Tetroxoprim and Trimethoprim;

Nitrofurans such as Furaltadone, Furazolium Chloride, Nifuradene, Nifuratel, Nifurfoline, Nifurpirinol, Nifurprazine, Nifurtoinol and Nitrofurantoin;

Quinolones and Analogs such as Amifloxacin, Cinoxacin, Ciprofloxacin, Difloxacin, Enoxacin, Fleroxacin, Flumequine, Lomefloxacin, Mioxacin, Nalidixic Acid, Norfloxacin, Ofloxacin, Oxolinic Acid, Pefloxacin, Pipemidic Acid, Piromidic Acid, Rosoxacin, Temafloxacin and Tosufloxacin;

Sulfonamides such as Acetyl Sulfamethoxypyrazine, Acetyl Sulfisoxazole, Azosulfamide, Benzylsulfamide, Chloramine-B, Chloramine-T, Dichloramine T, Formosulfathiazole, $N^2$ Formylsulfisomidine, $N^2$-a-D-Glucosylsulfanilamide, Mafenide, 4'-(Methylsulfamoyl)sulfanilanilide, p-Nitrosulfathiazole, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, Sulfamidochrysoidine, Sulfamoxole, Sulfanilamide, Sulfanilamidomethanesulfonic Acid Triethanolamine Salt, 4-Sulfanilamidosalicylic Acid, N$^4$-Sulfanilylsulfanilamide, Sulfanilylurea, N-Sulfanilyl-3, 4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine and Sulfisoxazole;

Sulfones such as Acedapsone, Acediasulfone, Acetosulfone Sodium, Dapsone, Diathymosulfone, Glucosulfone Sodium, Solasulfone, Succisulfone, Sulfanilic Acid, p-Sulfanilylbenzylamine, p,p'-Sulfonyldianiline-N,N' digalactoside, Sulfoxone Sodium and Thiazolsulfone; and others such as Clofoctol, Hexedine, Methenamine, Methenamine Anhydromethylene-citrate, Methenamine Hippurate, Methenamine Mandelate, Methenamine Sulfosalicylate, Nitroxoline and Xibornol, Anticholinergics such as Adiphenine Hydrochloride, Alverine, Ambutonomium Bromide, Aminopentamide, Amixetrine, Amprotropine Phosphate, Anisotropine Methylbromide, Apoatropine, Atropine, Atropine N-Oxide, Benactyzine, Benapryzine, Benzetimide, Benzilonium Bromide, Benztropine Mesylate, Bevonium Methyl Sulfate, Biperiden, Butropium Bromide, N-Butylscopolammonium Bromide, Buzepide, Camylofine, Caramiphen Hydrochloride, Chlorbenzoxamine, Chlorphenoxamine, Cimetropium Bromide, Clidinium Bromide, Cyclodrine, Cyclonium Iodide, Cycrimine Hydrochloride, Deptropine, Dexetimide, Dibutoline Sulfate, Dicyclomine Hydrochloride, Diethazine, Difemerine, Dihexyverine, Diphemanil Methylsulfate, N-(1, 2-Diphenylethyl)nicotinamide, Dipiproverine, Diponium Bromide, Emepronium Bromide, Endobenzyline Bromide, Ethopropazine, Ethybenztropine, Ethylbenzhydramine, Etomidoline, Eucatropine, Fenpiverinium Bromide, Fentonium Bromide, Flutropium Bromide, Glycopyrrolate, Heteronium Bromide, Hexocyclium Methyl Sulfate, Homatropine, Hyoscyamine, Ipratropium Bromide, Isopropamide, Levomepate, Mecloxamine, Mepenzolate Bromide, Metcaraphen, Methantheline Bromide, Methixene, Methscopolamine Bromide, Octamylamine, Chloride, Oxyphencyclimine, Oxyphenonium Bromide, Pentapiperide, Penthienate Bromide, Phencarbamide, Phenglutarimide, Pipenzolate Bromide, Piperidolate, Piperilate, Poldine Methysulfate, Pridinol, Prifinium Bromide, Procyclidine, Propantheline Bromide, Propenzolate, Propyromazine, Scopolamine, Scopolamine N-Oxide, Stilonium Iodide, Stramonium, Sultroponium, Thihexinol, Thiphenamil, Tiemonium Iodide, Timepidium Bromide, Tiquizium Bromide, Tridihexethyl Iodide, Trihexyphenidyl Hydrochloride, Tropacine, Tropenzile, Tropicamide, Trospium Chloride, Valethamate Bromide and Xenylropium Bromide.

28. Anticonvulsants such as Acetylpheneturide, Albutoin, Aloxidone, Aminoglutethimide, 4-Amino-3-hydroxybutyric Acid, Atrolactamide, Beclamide, Buramate, Calcium Bromide, Carbamazepine, Cinromide, Clomethiazole, Clonazepam, Decimemide, Diethadione, Dimethadione, Doxenitoin, Eterobarb, Ethadione, Ethosuximide, Ethotoin, Fluoresone, Garbapentin, 5-Hydroxytryptophan, Lamotrigine, Lomactil, Magnesium Bromide, Magnesium Sulfate, Mephenyloin, Mephobarbital, Metharbital, Methetoin, Methsuximide, 5-Methyl-5-(3-phenanthryl)hydantoin, 3-Methyl-5-phenylhydantoin, Narcobarbital, Nimetazepam, Nitrazepam, Paramethadione, Phenacemide, Phenetharbital, Pheneturide, Phenobarbital, Phenobarbital Sodium, Phensuximide, Phenylmethylbarbituric Acid, Phenyloin, Phethenylate Sodium, Potassium Bromide, Pregabatin, Primidone, Progabide, Sodium Bromide, Sodium Valproate, Solanum, Strontium Bromide, Suclofenide, Sulthiame, Tetrantoin, Tiagabine, Trimethadione, Valproic Acid, Valpromide, Vigabatrin and Zonisamide.

29. Antidepressants, including:

Bicyclics such as Binedaline, Caroxazone, Citalopram, Dimethazan, Indalpine, Fencamine, Indeloxazine Hydrochcloride, Nefopam, Nomifensine, Oxitriptan, Oxypertine, Paroxetine, Sertraline, Thiazesim, Trazodone, Venlafaxine and Zometapine;

Hydrazides/Hydrazines such as Benmoxine, Iproclozide, Iproniazid, Isocarboxazid, Nialamide, Octamoxin and Phenelzine; Pyrrolidones such as Cotinine, Rolicyprine and Rolipram;

Tetracyclics such as Maprotiline, Metralindole, Mianserin and Oxaprotiline.

Tricyclics such as Adinazolam, Amitriptyline, Amitriptylinoxide, Amoxapine, Butriptyline, Clomipramine, Demexiptiline, Desipramine, Dibenzepin, Dimetracrine, Dothiepin, Doxepin, Fluacizine, Imipramine, Imipramine N-Oxide, Iprindole, Lofepramine, Melitracen, Metapramine, Nortriptyline, Noxiptilin, Opipramol, Pizotyline, Propizepine, Protriptyline, Quinupramine, Tianeptine and Trimipramine; and others such as Adrafinil, Benactyzine, Bupropion, Butacetin, Deanol, Deanol Aceglumate, Deanol Acetamidobenzoate, Dioxadrol, Etoperidone, Febarbamate, Femoxetine, Fenpentadiol, Fluoxetine, Fluvoxamine, Fluvoxamine Maleate, Hematoporphyrin, Hypercinin, Levophacetoperane, Medifoxamine, Minaprine, Moclobemide, Oxaflozane, Piberaline, Prolintane, Pyrisuccideanol, Rubidium Chloride, Sulpiride, Sultopride, Teniloxazine, Thozalinone, Tofenacin, Toloxatone, Tranylcypromine, L-Tryptophan, Viloxazine and Zimeldine.

30. Antidiabetics, including:

Biguanides such as Buformin, Metformin and Phenformin;

Hormones such as Glucagon and Insulin;

Sulfonylurea derivatives such as Acetohexamide, 1-Butyl-3-metanilylurea, Carbutamide, Chlorpropamide, Glibornuride, Gliclazide, Glipizide, Gliquidone, Glisoxepid, Glyburide, Glybuthiazol(e), Glybuzole, Glyhexamide, Glymidine, Glypinamide, Phenbutamide, Tolazamide, Tolbutamide and Tolcyclamide; and others such as Acarbose, Calcium Mesoxalate and Miglitol.

31. Antidiarrheal drugs such as Acetyltannic Acid, Albumin Tannate, Alkofanone, Aluminum Salicylates—Basic, Catechin, Difenoxin, Diphenoxylate, Lidamidine, Lomotil, Loperamide, Mebiquine, Trillium and Uzarin.

32. Antidiuretics such as Desmopressin, Felypressin, Lypressin, Ornipressin, Oxycinchophen, Pituitary—Posterior, Terlipressin and Vasopressin.

33. Antiestrogens such as Delmadinone Acetate, Ethamoxytriphetol, Tamoxifen and Toremifene.

34. Antifungal drugs (antibiotics), including:

Polyenes such as Amphotericin-B, Candicidin, Dermostatin, Filipin, Fungichromin, Hachimycin, Hamycin, Lucensomycin, Mepartricin, Natamycin, Nystatin, Pecilocin and Perimycin; and others such as Azaserine, Griseofulvin, Oligomycins, Neomycin Undecylenate, Pyrrolnitrin, Siccanin, Tubercidin and Viridin.

35. Antifungal drugs (synthetic), including:

Allylamines such as Naftifine and Terbinafine;

Imidazoles such as Bifonazole, Butoconazole, Chlordantoin, Chlormidazole, Cloconazole, Clotrimazole, Econazole, Enilconazole, Fenticonazole, Isoconazole, Ketoconazole, Miconazole, Omoconazole, Oxiconazole, Nitrate, Sulconazole and Tioconazole;

Triazoles such as Fluconazole, Itraconazole and Terconazole; and others such as Acrisorcin, Amorolfine, Biphenamine, Bromosalicylchloranilide, Buclosamide, Calcium Propionate, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Tolciclate, Tolindate, Tolnaftate, Tricetin, Ujothion, Undecylenic Acid and Zinc Propionate.

36. Antiglaucoma drugs such as Acetazolamide, Befunolol, Betaxolol, Bupranolol, Carteolol, Dapiprazole, Dichlorphenamide, Dipivefrin, Epinephrine, Levobunolol, Methazolamide, Metipranolol, Pilocarpine, Pindolol and Timolol.

37. Antigonadotropins such as Danazol, Gestrinone and Paroxypropione.

38. Antigout drugs such as Allopurinol, Carprofen, Colchicine, Probenecid and Sulfinpyrazone.

39. Antihistamines, including:

Alkylamine derivatives such as Acrivastine, Bamipine, Brompheniramine, Chlorpheniramine, Dimethindene, Metron S, Pheniramine, Pyrrobutamine, Thenaldine, Tolpropamine and Triprolidine;

Aminoalkyl ethers such as Bietanautine, Bromodiphenhydramine, Carbinoxamine, Clemastine, Diphenlypyraline, Doxylamine, Embramine, Medrylamine, Mephenphydramine, p-Methyldiphenhydramine, Orphenadrine, Phenyltoloxamine, Piprinhydrinate and Setasine;

Ethylenediamine derivatives such as Alloclamide, p-Bromtripelennamine, Chloropyramine, Chlorothen, Histapyrrodine, Methafurylene, Methaphenilene, Methapyrilene, Phenbenzamine, Pyrilamine, Talastine, Thenyldiamine, Thonzylamine Hydrochloride, Tripelennamine and Zolamine;

Piperazines such as Cetirizine, Chlorcyclizine, Cinnarizine, Clocinizine and Hydroxyzine;

Tricyclics, including:

Phenothiazines such as Ahistan, Etymemazine, Fenethazine, N-Hydroxyethylpromethazine Chloride, Isopromethazine, Mequitazine, Promethazine, Pyrathiazine and Thiazinamium Methyl Sulfate; and others such as Azatadine, Clobenzepam, Cyproheptadine, Deptropine, Isothipendyl, Loratadine and Prothipendyl; and other antihistamines such as Antazoline, Astemizole, Azelastine, Cetoxime, Clemizole, Clobenztropine, Diphenazoline, Diphenhydramine, Fluticasone Propionate, Mebhydroline, Phenindamine, Terfenadine and Tritoqualine.

40. Antihyperlipoproteinemics, including:

Aryloxyalkanoic acid derivatives such as Beclorbrate, Bazafibrate, Binifibrate, Ciprofibrate, Clinofibrate, Clofibrate, Clofibric Acid, Etonfibrate, Fenofibrate, Gemfibrozil, Nicofibrate, Pirifibrate, Ronifibrate, Simfibrate and Theofibrate;

Bile acid sequesterants such as Cholestyramine Resin, Colestipol and Polidexide;

HMG CoA reductase inhibitors such as Fluvastatin, Lovastatin, Pravastatin Sodium and Simvastatin;

Nicotinic acid derivatives Aluminum Nicotinate, Acipimox, Niceritrol, Nicoclonate, Nicomol and Oxiniacic Acid;

Thyroid hormones and analogs such as Etiroxate, Thyropropic Acid and Thyroxine; and others such as Acifran, Azacosterol, Benfluorex, a-Benzalbutyramide, Carnitine, Chondroitin Sulfate, Clomestone, Detaxtran, Dextran Sulfate Sodium, 5,8,11,14,17-Eicosapentaenoic Acid, Eritadenine, Furazbol, Meglutol, Melinamide, Mytatrienediol, Ornithine, a-Oryzanol, Pantethine, Penataerythritol Tetraacetate, a-Phenylbutyramide, Pirozadil, Probucol, a-Sitosterol, Sultosilic Acid, piperazine Salt, Tiadenol, Triparanol and Xenbucin.

41. Antihypertensive drugs, including:

Arylethanolamine derivatives such as Amosulalol, Bufuralol, Dilevalol, Labetalol, Pronethalol, Sotalol and Sulfinalol;

Aryloxypropanolamine derivatives such as Acebutolol, Alprenolol, Arotinolol, Atenolol, Betaxolol, Bevantolol, Bisoprolol, Bopindolol, Bunitrolol, Bupranolol, Butofilolol, Carazolol, Cartezolol, Carvedilol, Celiprolol, Cetamolol, Epanolol, Indenolol, Mepindolol, Metipranolol, Metoprolol, Moprolol, Nadolol, Nipradilol, Oxprenolol, Penbutolol, Pindolol, Propranolol, Talinolol, Tetraolol, Timolol and Toliprolol;

Benzothiadiazine derivatives such as Althiazide, Bendroflumethiazide, Benzthiazide, Benzylhydrochlorothiazide, Buthiazide, Chlorothiazide, Chlorthalidone, Cyclopenthiazide, Cyclothiazide, Diazoxide, Epithiazide, Ethiazide, Fenquizone, Hydrochlorothiazide, Hydroflumethiazide, Methyclothiazide, Meticrane, Metolazone, Paraflutizide, Polythiazide, Tetrachlormethiazide and Trichlormethiazide;

N-Carboxyalkyl (peptide/lactam) derivatives such as Alacepril, Captopril, Cilazapril, Delapril, Enalapril, Enalaprilat, Fosinopril, Lisinopril, Moveltipril, Perindopril, Quinapril and Ramipril;

Dihydropyridine derivatives such as Amlodipine, Felodipine, Isradipine, Nicardipine, Nifedipine, Nilvadipine, Nisoldipine and Nitrendipine;

Guanidine derivatives such as Bethanidine, Debrisoquin, Guanabenz, Guanacline, Guanadrel, Guanazodine, Guanethidine, Guanfacine, Guanochlor, Guanoxabenz and Guanoxan;

Hydrazines and phthalazines such as Budralazine, Cadralazine, Dihydralazine, Endralazine, Hydracarbazine, Hydralazine, Pheniprazine, Pildralazine and Todralazine;

Imidazole derivatives such as Clonidine, Lofexidine, Phentolamine, Phentolamine Mesylate, Tiamenidine and Tolonidine;

Quaternary ammonium compounds Azamethonium Bromide, Chlorisondamine Chloride, Hexamethonium, Pentacynium Bis(methyl sulfate), Pentamethonium Bromide, Pentolinium Tartate, Phenactopinium Chloride and Trimethidiunum Methosulfate;

Quinazoline derivatives such as Alfuzosin, Bunazosin, Doxazosin, Prasosin, Terazosin and Trimazosin;

Reserpine derivatives such as Bietaserpine, Deserpidine, Rescinnamine, Reserpine and Syrosingopine;

Sulfonamide derivatives such as Ambuside, Clopamide, Furosemide, Indapamide, Quinethazone, Tripamide and Xipamide; and others such as Ajmaline, a-Aminobutyric Acid, Bufeniode, Candesartan, Chlorthalidone, Cicletaine, Ciclosidomine, Cryptenamine Tannates, Eprosartan, Fenoldopam, Flosequinan, Indoramin, Irbesartan, Ketanserin, Losartan, Metbutamate, Mecamylamine, Methyldopa, Methyl 4-Pyridyl Ketone Thiosemicarbarzone, Metolazone, Minoxidil, Muzolimine, Pargyline, Pempidine, Pinacidil, Piperoxan, Primaperone, Protoveratrines, Raubasine, Rescimetol, Rilmenidene, Saralasin, Sodium Nitroprusside, Ticrynafen, Trimethaphan Camsylate, Tyrosinase, Urapidil and Valsartan.

42. Antihyperthyroids such as 2-Amino-4-methylthiazole, 2-Aminothiazole, Carbimazole, 3,5-Dibromo-L-tyrosine, 3,5-Diiodotyrosine, Hinderin, Iodine, Iothiouracil, Methimazole, Methylthiouracil, Propylthiouracil, Sodium Perchlorate, Thibenzazoline, Thiobarbital and 2-Thiouracil.

43. Antihypotensive drugs such as Amezinium Methyl Sulfate, Angiotensin Amide, Dimetofrine, Dopamine, Etifelmin, Etilefrin, Gepefrine, Metaraminol, Midodrine, Norepinephrine, Pholedrinead and Synephrine.

44. Antihypothyroid drugs such as Levothyroxine Sodium, Liothyronine, Thyroid, Thyroidin, Thyroxine, Tiratricol and TSH.

45. Anti-Inflammatory (non-steroidal) drugs, including:

Aminoarylcarboxylic acid derivatives such as Enfenamic Acid, Etofenamate, Flufenamic Acid, Isonixin, Meclofenamic Acid, Mefanamic Acid, Niflumic Acid, Talniflumate, Terofenamate and Tolfenamic Acid;

Arylacetic acid derivatives such as Acemetacin, Alclofenac, Amfenac, Bufexamac, Cinmetacin, Clopirac, Diclofenac Sodium, Etodolac, Felbinac, Fenclofenac, Fenclorac, Fenclozic Acid, Fentiazac, Glucametacin, Ibufenac, Indomethacin, Isofezolac, Isoxepac, Lonazolac, Metiazinic Acid, Oxametacine, Proglumetacin, Sulindac, Tiaramide, Tolmetin and Zomepirac;

Arylbutyric acid derivatives such as Bumadizon, Butibufen, Fenbufen and Xenbucin;

Arylcarboxylic acids such as Clidanac, Ketorolac and Tinoridine;

Arylpropionic acid derivatives such as Alminoprofen, Benoxaprofen, Bucloxic Acid, Carprofen, Fenoprofen, Flunoxaprofen, Flurbiprofen, Ibuprofen, Ibuproxam, Indoprofen, Ketoprofen, Loxoprofen, Miroprofen, Naproxen, Oxaprozin, Piketoprofen, Pirprofen, Pranoprofen, Protizinic Acid, Suprofen and Tiaprofenic Acid;

Pyrazoles such as Difenamizole and Epirizole;

Pyrazolones such as Apazone, Benzpiperylon, Feprazone, Mofebutazone, Morazone, Oxyphenbutazone, Phenybutazone, Pipebuzone, Propyphenazone, Ramifenazone, Suxibuzone and Thiazolinobutazone;

Salicylic acid derivatives such as Acetaminosalol, Aspirin, Benorylate, Bromosaligenin, Calcium Acetylsalicylate, Diflunisal, Etersalate, Fendosal, Gentisic Acid, Glycol Salicylate, Imidazole Salicylate, Lysine Acetylsalicylate, Mesalamine, Morpholine Salicylate, 1-Naphthyl Salicylate, Olsalazine, Parsalmide, Phenyl Acetylsalicylate, Phenyl Salicylate, Salacetamide, Salicylamine O-Acetic Acid, Salicylsulfuric Acid, Salsalate and Sulfasalazine;

Thiazinecarboxamides such as Droxicam, Isoxicam, Piroxicam and Tenoxicam; and others such as ε-Acetamidocaproic Acid, S-Adenosylmethionine, 3-Amino-4-hydroxybutyric Acid, Amixetrine, Bendazac, Benzydamine, Bucolome, Difenpiramide, Ditazol, Emorfazone, Guaiazulene, Nabumetone, Nimesulide, Orgotein, Oxaceprol, Paranyline, Perisoxal, Pifoxime, Proquazone, Proxazole and Tenidap.

46. Antimalarial drugs such as Acedapsone, Amodiaquin, Arteether, Artemether, Artemisinin, Artesunate, Bebeerine, Berberine, Chirata, Chlorguanide, Chloroquine, Chlorproguanil, Cinchona, Cinchonidine, Cinchonine, Cycloguanil, Gentiopicrin, Halofantrine, Hydroxychloroquine, Mefloquine Hydrochloride, 3-Methylarsacetin, Pamaquine, Plasmocid, Primaquine, Pyrimethamine, Quinacrine, Quinine, Quinine Bisulfate, Quinine Carbonate, Quinine Dihydrobromide, Quinine Dihydrochloride, Quinine Ethylcarbonate, Quinine Formate, Quinine Gluconate, Quinine Hydriodide, Quinine Hydrochloride, Quinine Salicylate, Quinine Sulfate, Quinine Tannate, Quinine Urea Hydrochloride, Quinocide, Quinoline and Sodium Arsenate Diabasic.

47. Antimigraine drugs such as Alpiropride, Dihydroergotamine, Eletriptan, Ergocornine, Ergocominine, Ergocryptine, Ergot, Ergotamine, Flumedroxone acetate, Fonazine, Lisuride, Methysergid(e), Naratriptan, Oxetorone, Pizotyline, Rizatriptan and Sumatriptan.

48. Antinauseant drugs such as Acetylleucine Monoethanolamine, Alizapride, Benzquinamide, Bietanautine, Bromopride, Buclizine, Chlorpromazine, Clebopride, Cyclizine, Dimenhydrinate, Dipheniodol, Domperidone, Granisetron, Meclizine, Methalltal, Metoclopramide, Metopimazine, Nabilone, Ondansteron, Oxypendyl, Pipamazine, Piprinhydrinate, Prochlorperazine, Scopolamine, Tetrahydrocannabinols, Thiethylperazine, Thioproperzaine and Trimethobenzamide.

49. Antineoplastic drugs, including:

Alkylating agents, including:

Alkyl sulfonates such as Busulfan, Improsulfan and Piposulfan;

Aziridines such as Benzodepa, Carboquone, Meturedepa and Uredepa;

Ethylenimines and methylmelamines such as Altretamine, Sulfosamide, Triethylenemelamine, Triethylenephosphoramide, Triethylenethiophosphoramide and Trimethylolomelamine;

Nitrogen mustards such as Chlorambucil, Chlornaphazine, Chclophosphamide, Estramustine, Ifosfamide, Mechlorethamine, Mechlorethamine Oxide Hydrochloride, Melphalan, Novembichin, Phenesterine, Prednimustine, Trofosfamide and Uracil Mustard;

Nitrosoureas such as Carmustine, Chlorozotocin, Fotemustine, Lomustine, Nimustine and Ranimustine; and others such as Camptothecin, Dacarbazine, Mannomustine, Mitobronitol, Mitolactol and Pipobroman;

Antibiotics such as Aclacinomycins, Actinomycin Ft, Anthramycin, Azaserine, Bleomycins, Cactinomycin, Carubicin, Carzinophilin, Chromomycins, Dactinomycin, Daunorubicin, 6-Diazo-5-oxo-L-norleucine, Doxorubicin, Epirubicin, Mitomycins, Mycophenolic Acid, Nogalamycin, Olivomycins, Peplomycin, Plicamycin, Porfiromycin, Puromycin, Rufocromomycin, Streptonigrin, Streptozocin, Tubercidin, Ubenimex, Zinostatin and Zorubicin;

Antimetabolites, including:

Folic acid analogs such as Denopterin, Methotrexate, Pteropterin and Trimetrexate;

Purine analogs such as Fludarabine, 6-Mercaptopurine, Thiamiprine and Thioguanaine; and Pyrimidine analogs such as Ancitabine, Azacitidine, 6-Azauridine, Carmofur, Cytarabine, Doxifluridine, Enocitabine, Floxuridine, Fluoroouracil and Tegafur;

Enzymes such as L-Asparaginase; and others such as Aceglatone, Amsacrine, Bestrabucil, Bisantrene, Bryostatin 1, Carboplatin, Cisplatin, Defofamide, Demecolcine, Diaziquone, Dolastatins, Elfomithine, Elliptinium Acetate, Etoglucid, Etoposide, Gallium Nitrate, Hydroxyurea, Interferon-a, Interferon-a, Interferon-a, Interleukine-2, Lentinan, Letrozole, Lonidamine, Mitoguazone, Mitoxantrone, Mopidamol, Nitracrine, Pentostatin, Phenamet, Pirarubicin, Podophyllinicc Acid, 2-Ethylhydrazide, Polynitrocubanes, Procarbazine, PSK7, Razoxane, Sizofuran, Spirogermanium, Symplostatin 1, Taxol, Teniposide, Tenuazonic Acid, Triaziquone, 2,2',2''-Trichlorotriethylamine, Urethan, Vinblastine, Vincristine, Vindesine and Vinorelbine.

50. Antineoplastic (hormonal) drugs, including:
Androgens such as Calusterone, Dromostanolone Propionate, Epitiostanol, Mepitiostane and Testolactone;
Antiadrenals such as Aminoglutethimide, Mitotane and Trilostane;
Antiandrogens such as Flutamide and Nilutamide; and
Antiestrogens such as Tamoxifen and Toremifene.

51. Antineoplastic adjuncts including folic acid replenishers such as Frolinic Acid.

52. Antiparkinsonian drugs such as Amantadine, Apomorphine, Benserazide, Bietanautine, Biperiden, Bromocriptine, Budipine, Cabergoline, Carbidopa, Dexetimide, Diethazine, Diphenhydramine, Droxidopa, Ethopropazine, Ethylbenzhydramine, Levodopa, Naxagolide, Pergolide, Piroheptine, Pramipexole, Pridinol, Prodipine, Quinpirole, Remacemide, Ropinirole, Terguride, Tigloidine and Trihexyphenidyl Hydrochloride.

53. Antipheochromocytoma drugs such as Metyrosine, Phenoxybenzamine and Phentolamine.

54. Antipneumocystis drugs such as Effornithine, Pentamidine and Sulfamethoxazole.

55. Antiprostatic hypertrophydrugs such as Gestonorone Caproate, Mepartricin, Oxendolone and Proscar7.

56. Antiprotozoal drugs (Leshmania) such as Antimony Sodium Gluconate, Ethylstibamine, Hydroxystilbamidine, N-Methylglucamine, Pentamidine, Stilbamidine and Urea Stibamine.

57. Antiprotozoal drugs (Trichomonas) such as Acetarsone, Aminitrozole, Anisomycin, Azanidazole, Forminitrazole, Furazolidone, Hachimycin, Lauroguadine, Mepartricin, Metronidazole, Nifuratel, Nifuroxime, Nimorazole, Secnidazole, Silver Picrate, Tenonitrozole and Tinidazole.

58. Antiprotozoal drugs (Trypanosma) such as Benznidazole, Eflornithine, Melarsoprol, Nifurtimox, Oxophenarsine, Hydrochloride, Pentamidine, Propamidine, Puromycin, Quinapyramine, Stilbamidine, Suramin Sodium, Trypan Red and Tryparasmide.

59. Antipuritics such as Camphor, Cyproheptadine, Dichlorisone, Glycine, Halometasone, 3-Hydroxycamphor, Menthol, Mesulphen, Methdilazine, Phenol, Polidocanol, Risocaine, Spirit of Camphor, Thenaldine, Tolpropamine and Trimeprazine.

60. Antipsoriatic drugs such as Acitretin, Ammonium Salicylate, Anthralin, 6-Azauridine, Bergapten(e), Chrysarobin, Etretinate and Pyrogallol.

61. Antipsychotic drugs, including:
Butyrophenones such as Benperidol, Bromperidol, properidol, Fluanisone, Haloperidol, Melperone, Moperone, Pipamperone, Sniperone, Timiperone and Trifluperidol;
Phenothiazines such as Acetophenazine, Butaperazine, Carphenazine, Chlorproethazine, Chlorpromazine, Clospirazine, Cyamemazine, Dixyrazine, Fluphenazine, Imiclopazine, Mepazine, Mesoridazine, Methoxypromazine, Metofenazate, Oxaflumazine, Perazine, Pericyazine, Perimethazine, Perphenazine, Piperacetazine, Pipotiazine, Prochlorperazine, Promazine, Sulforidazine, Thiopropazate, Thioridazine, Trifluoperazine and Triflupromazine;
Thioxanthenes such as Chlorprothixene, Clopenthixol, Flupentixol and Thiothixene;
other tricyclics such as Benzquinamide, Carpipramine, Clocapramine, Clomacran, Clothiapine, Clozapine, Opipramol, Prothipendyl, Tetrabenazine, and Zotepine; and
others such as Alizapride, Amisulpride, Buramate, Fluspirilene, Molindone, Penfluridol, Pimozide, Spirilene and Sulpiride.

62. Antipyretics such as Acetaminophen, Acetaminosalol, Acetanilide, Aconine, Aconite, Aconitine, Alclofenac, Aluminum Bis(acetylsalicylate), Aminochlorthenoxazin, Aminopyrine, Aspirin, Benorylate, Benzydamine, Berberine, p-Bromoacetanilide, Bufexamac, Burnadizon, Calcium Acetysalicylate, Chlorthenoxazin(e), Choline Salicylate, Clidanac, Dihydroxyaluminum Acetylsalicylate, Dipyrocetyl, Dipyrone, Epirizole, Etersalate, Imidazole Salicylate, Indomethacin, Isofezolac, p-Lactophenetide, Lysine Acetylsalicylate, Magnesium Acetylsalicylate, Meclofenamic Acid, Morazone, Morpholine Salicylate, Naproxen, Nifenazone, 5'-Nitro-2'-propoxyacetanilide, Phenacetin, Phenicarbazide, Phenocoll, Phenopyrazone, Phenyl Acetylsalicylate, Phenyl Salicylate, Pipebuzone, Propacetamol, Propyphenazone, Ramifenazone, Salacetamide, Salicylamide O-Acetic Acid, Sodium Salicylate, Sulfamipyrine, Tetrandrine and Tinoridine.

63. Antirickettsial drugs such as p-Aminobenzoic Acid, Chloramphenicol, Chloramphenicol Palmitate, Chloramphenicol Pantothenate and Tetracycline.

64. Antiseborrheic drugs such as Chloroxine, 3-O-Lauroylpyridoxol Diacetate, Piroctone, Pyrithione, Resorcinol, Selenium Sulfides and Tioxolone.

65. Antiseptics, including:
Guanidines such as Alexidine, Ambazone, Chlorhexidine and Picloxydine;
Halogens and halogen compounds such as Bismuth Iodide Oxide, Bismuth Iodosubgallate, Bismuth Tribromophenate, Bornyl Chloride, Calcium Iodate, Chlorinated Lime, Cloflucarban, Fluorosalan, Iodic Acid, Iodine, Iodine Monochloride, Iodine Trichloride, Iodoform, Methenamine Tetraiodine, oxychlorosene, Povidone-Iodine, Sodium Hypochlorite, Sodium Iodate, Symclosene, Thymol Iodide, Triclocarban, Triclosan and Troclosene Potassium;
Mercurial compounds such as Hydragaphen, Meralein Sodium, Merbromin, Mercuric Chloride, Mercuric Chloride, Ammoniated, Mercuric Sodium p-Phenolsulfonate, Mercuric Succinimide, Mercuric Sulfide, Red, Mercurophen, Mercurous Acetate, Mercurous Chloride, Mercurous Iodide, Nitromersol, Potassium Tetraiodomercurate(II), Potassium Triiodomercurate(II) Solution, Thimerfonate Sodium and Thimerosal;
Nitrofurans such as Furazolidone, 2-(Methoxymethyl)-5-nitrofuran, Nidroxyzone, Nifuroxime, Nifurzide and Nitrofurazone;
Phenols such as Acetomeroctol, Bithionol, Cadmium Salicylate, Carvacrol, Chloroxylenol, Clorophene, Cresote, Cresol(s), p-Cresol, Fenticlor, Hexachlorophene, 1-Napthyl Salicylate, 2-Napthyl Salicylate, 2,4,6-Tribromo-m-cresol, and 3',4',5-Trichlorosalicylanilide;
Quinolines such as Aminoquinuride, Benzoxiquine, Broxyquinoline, Chloroxine, Chlorquinaldol, Cloxyquin, Ethylhydrocupreine, Euprocin, Halquinol, Hydrastine, 8-Hydroxquinoline, 8-Hydroxyquinoline Sulfate and Iodochlorhydroxyquin; and
others such as Aluminum Acetate Solution, Aluminum Subacetate Solution, Aluminum Sulfate, 3-Amino-4-hydroxybutyric Acid, Boric Acid, Chlorhexidine, Chloroazodin, m-Cresyl Acetate, Cupric Sulfate, Dibromopropamidine, Ichthammol, Negatol7, Noxytiolin, Omidazole, a-Propiolactone, a-Terpineol.

66. Antispasmodic drugs such as Alibendol, Ambucetamide, Aminopromazine, Apoatropine, Bevonium Methyl Sulfate, Bietamiverine, Butaverine, Butropium Bromide, N-Butylscopolammonium Bromide, Caroverine, Cimetropium Bromide, Cinnamedrine, Clebopride, Coniine Hydrobromide, Coniine Hydrochloride, Cyclonium Iodide, Difemerine, Diisopromine, Dioxaphetyl Butyrate, Diponium Bromide, Drofenine, Emepronium Bromide, Ethaverine, Feclemine, Fenalamide, Fenoverine, Fenpiprane, Fenpiverinium Bromide, Fentonium Bromide, Flavoxate, Flopropione, Gluconic Acid, Guaiactamine, Hydramitrazine, Hymecromone, Leiopyrrole, Mebeverine, Moxaverine, Nafiverine, Octamylamine, Octaverine, Pentapiperide, Phenamacide Hydrochloride, Phloroglucinol, Pinaverium Bromide, Piperilate, Pipoxolan Hydrochloride, Pramiverin, Prifinium Bromide, Properidine, Propivane, Propyromazine, Prozapine, Racefemine, Rociverine, Spasmolytol, Stilonium Iodide, Sultroponium, Tiemonium Iodide, Tiquizium Bromide, Tiropramide, Trepibutone, Tricromyl, Trifolium, Trimebutine, N,N-1Trimethyl-3,3-diphenyl-propylamine, Tropenzile, Trospium Chloride and Xenylropium Bromide.

67. Antithrombotic drugs such as Anagrelide, Argatroban, Cilostazol, Chrysoptin, Daltroban, Defibrotide, Enoxaparin, Fraxiparine7, Indobufen, Lamoparan, Ozagrel, Picotamide, Plafibride, Reviparin, Tedelparin, Ticlopidine, Triflusal and Warfarin.

68. Antitussive drugs such as Allocamide, Amicibone, Benproperine, Benzonatate, Bibenzonium Bromide, Bromoform, Butamirate, Butethamate, Caramiphen Ethanedisulfonate, Carbetapentane, Chlophedianol, Clobutinol, Cloperastine, Codeine, Codeine Methyl Bromide, Codeine N-Oxide, Codeine Phosphate, Codeine Sulfate, Cyclexanone, Dextromethorphan, Dibunate Sodium, Dihydrocodeine, Dihydrocodeinone Enol Acetate, Dimemorfan, Dimethoxanate, a,a-Diphenyl-2-piperidinepropanol, propropizine, Drotebanol, Eprazinone, Ethyl Dibunate, Ethylmorphine, Fominoben, Guiaiapate, Hydrocodone, Isoaminile, Levopropoxyphene, Morclofone, Narceine, Normethadone, Noscapine, Oxeladin, Oxolamine, Pholcodine, Picoperine, Pipazethate, Piperidione, Prenoxdiazine Hydrochloride, Racemethorphan, Taziprinone Hydrochloride, Tipepidine and Zipeprol.

69. Antiulcerative drugs such as Aceglutamide Aluminum Complex, ε-Acetamidocaproic Acid Zinc Salt, Acetoxolone, Arbaprostil, Benexate Hydrochloride, Bismuth Subcitrate Sol (Dried), Carbenoxolone, Cetraxate, Cimetidine, Enprostil, Esaprazole, Famotidine, Ftaxilide, Gefamate, Guaiazulene, Irsogladine, Misoprostol, Nizatidine, Omeprazole, Ornoprostil, a-Oryzanol, Pifamine, Pirenzepine, Plaunotol, Ranitidine, Rioprostil, Rosaprostol, Rotraxate, Roxatidine Acetate, Sofalcone, Spizofurone, Sucralfate, Teprenone, Trimoprostil, Thrithiozine, Troxipide and Zolimidine.

70. Antiurolithic drugs such as Acetohydroxamic Acid, Allopurinol, Potassium Citrate and Succinimide.

71. Antivenin drugs such as Lyovac7 Antivenin.

72. Antiviral drugs, including:
Purines and pyrimidinones such as Acyclovir, Cytarabine, Dideoxyadenosine, Dideoxycytidine, Dideoxyinosine, Edoxudine, Floxuridine, Ganciclovir, Idoxuridine, Inosine Pranobex, MADU, Penciclovir, Trifluridine, Vidrarbine and Zidovudiine; and others such as Acetylleucine Monoethanolamine, Amantadine, Amidinomycin, Cosalane, Cuminaldehyde Thiosemicarbzone, Foscarnet Sodium, Imiquimod, Interferon-a, Interferon-a, Interferon-a, Kethoxal, Lysozyme, Methisazone, Moroxydine, Podophyllotoxin, Ribavirin, Rimantadine, Stallimycin, Statolon, Tromantadine and Xenazoic Acid.

73. Anxiolytic drugs, including:
Arylpiperazines such as Buspirone, Gepirone, Isapirone and Tondospirone.

Benzodiazepine derivatives such as Alprazolam, Bromazepam, Camazepam, Chlordiazepoxide, Clobazam, Clorazepate, Chotiazepam, Cloxazolam, Diazepam, Ethyl Loflazepate, Etizolam, Fluidazepam, Flutazolam, Flutoprazepam, Halazepam, Ketazolam, Lorazepam, Loxapine, Medazepam, Metaclazepam, Mexazolam, Nordazepam, Oxazepam, Oxazolam, Pinazepam, Prazepam and Tofisopam;

Carbamates such as Cyclarbamate, Emylcamate, Hydroxyphenamate, Meprobamate, Phenprobamate and Tybamate; and others such as Alpidem, Benzoctamine, Captodiamine, Chlormezanone, Etifoxine, Flesinoxan, Fluoresone, Glutamic Acid, Hydroxyzine, Lesopitron, Mecloralurea, Mephenoxalone, Mirtazepine, Oxanamide, Phenaglycodol, Suriclone and Zatosetron.

74. Benzodiazepine antagonists such as Flumazenil.

75. Bronchodilators, including:
Ephedrine derivatives such as Albuterol, Bambuterol, Bitolterol, Carbuterol, Clenbuterol, Clorprenaline, Dioxethedrine, Ephedrine, Epiniphrine, Eprozinol, Etafedrine, Ethylnorepinephrine, Fenoterol, Hexoprenaline, Isoetharine, Isoproterenol, Mabuterol, Metaproterenol, N-Methylephedrine, Pirbuterol, Procaterol, Protokylol, Reproterol, Rimiterol, Salmeterol, Soterenol, Terbutaline and Tulobuterol;

Quaternary ammonium compounds such as Bevonium Methyl Sulfate, Clutropium Bromide, Ipratropium Bromide and Oxitropium Bromide;

Xanthine derivatives such as Acefylline, Acefylline piperazine, Ambuphylline, Aminophylline, Bamifylline, choline Theophyllinate, Doxofylline, Dyphylline, Enprofylline, Etamiphyllin, Etofylline, Guaithylline, Proxyphylline, Theobromine, 1-Theobromineacetic Acid and Theophylline; and others such as Fenspiride, Medibazine, Montekulast, Methoxyphenanime, Tretoquinol and Zafirkulast.

76. Calcium channel blockers, including:
Arylalkylamines such as Bepridil, Ditiazem, Fendiline, Gallopanil, Prenylamine, Terodiline and Verapamil;

Dihydropyridine derivatives such as Felodipine, Isradipine, Nicardipine, Nifedipine, Nilvadipine, Nimodipine, Nisoldipine and Nitrendipine;

piperazine derivatives such as Cinnarizine, Flunarisine and Lidoflazine; and others such as Bencyclane, Etafenone and Perhexyline.

77. Calcium regulators such as Calcifediol, Calcitonin, Calcitriol, Clodronic Acid, Dihydrotachysterol, Elcatonin, Etidronic Acid, Ipriflavone, Pamidronic Acid, Parathyroid Hormone and Teriparatide Acetate.

78. Cardiotonics such as Acefylline, Acetyldigititoxins, 2-Amino-4-picoline, Amrinone, Benfurodil Hemisuccinate, Buclasdesine, Cerberoside, Camphotamide, Convallatoxin, Cymarin, Denopamine, Deslanoside, Ditalin, Digitalis, Digitoxin, Digoxin, Dobutamine, Dopamine, Dopexamine, Enoximone, Erythrophleine, Fenalcomine, Gitalin, Gitoxin, Glycocyamine, Heptaminol, Hydrastinine, Ibopamine, Lanotodises, Metamivam, Milrinone, Neriifolin, Oleandrin, Ouabain, Oxyfedrine, Prenalterol, Proscillaridin, Resibufogenin, Scillaren, Scillarenin, Strophanthin, Sulmazole, Theobromine and Xamoterol.

79. Chelating agents such as Deferozmine, Ditiocarb Sodium, Edetate Calcium Disodium, Edetate Disodium, Edeate Sodium, Edetate Trisodium, Penicillamine, Pentetate Calcium Trisodium, Pentectic Acid, Succimer and Trientine;

80. Cholecystokinin antagonists such as Proglumide.

81. Cholelitholytic agents such as Chenodiol, Methyl tert-Butyl Ether, Monooctanoin and Ursodiol.

82. Choleretics such as Alibendol, Anethole Trithion, Azintamide, Cholic Acid, Cicrotoic Acid, Clanobutin, Cyclobutyrol, Cyclovalone, Cynarin(e), Dehydrocholic Acid, Deoxycholic Acid, Dimecrotic Acid, a-Ethylbenzyl Alcohol, Exiproben, Feguprol, Fencibutirol, Fenipentol, Florantyrone, Hymecromone, Menbutone, 3-(o-Methyphenyl)-2-phenylacrylic Acid, Metochalcone, Moquizone, Osalmid, Ox Bile Extract, 4,4'-Oxydi-2-butanol, Piprozolin, Prozapine, 4-Salicyloylmorpholine, Sincalide, Taurocholic Acid, Timonacic, Tocamphyl, Trepibutone and Vanitiolide.

83. Cholinergic agents such as Aceclidine, Acetylcholine Bromide, Acetycholide Chloride, Aclatonium Napadisilate, Benzpyrinium Bromide, Bethanechol chloride, Carbachol, Carpronium chloride, Demecarium Bromide, Dexpanthenol, Diisopropyl Paraoxon, Echothiophate Iodide, Edrophomium chloride, Eseridine, Furtrethonium, Isofluorophate, Methacholine chloride, Muscarine, Neostigmine, Oxapropanium Iodide, Physostigmine and Pyridostigmine Bromide.

84. Cholinesterase inhibitors such as Ambenonium Chloride, Distigmine Bromide and Galanthamine.

85. Cholinesterase reactivators such as Obidoximine Chloride and Pralidoxime Chloride.

86. Central nervous system stimulants and agents such as Amineptine, Amphetiminie, Amphetaminil, Bemegride, Benzphetamine, Brucine, Caffeine, Chlorphentermine, Clofenciclan, Clortermine, Coca, Demanyl Phosphate, Dexoxadrol, Dextroamphetamine Sulfate, Diethlpropion, N-Ethylamphetamine, Ethamivan, Etifelmin, Etryptamine, Fencamfamine, Fenethylline, Fenosolone, Fluorothyl, Galanthamine, Hexacyclonate Sodium, Homocamfin, Mazindol, Megexamide, Methamphetamine, Methylphenidate, Nikethamide, Pemoline, Pentylenetetrazole, Phenidimetrazine, Phenmetrazine, Phentermine, Picrotoxin, Pipradrol, Prolintane and Pyrovalerone.

87. Decongestants such as Amidephrine, Cafaminol, Cyclopentamine, Ephedrine, Epinephrine, Fenoxazoline, Indanazoline, Metizoline, Naphazoline, Nordefrin Hydrochloride, Octodrine, Oxymetazoline, Phenylephrine Hydrochloride, Phenylpropanolamine Hydrochloride, Phenylpropylmethylamine, Propylhexedrine, Pseudoephedrine, Tetrahydrozoline, Tymazoline and Xylometazoline.

88. Dental agents, including:
Bisphosphonates (anti-periodontal disease and bone resorption) such as Alendronate, Clodronate, Etidronate, Pamidronate and Tiludronate;
Carries Prophylactics such as Arginine and Sodium Fluoride; Desensitizing Agents such as Potassium Nitrate and Citrate Oxalate.

89. Depigmentors such as Hydroquinine, Hydroquinone and Monobenzone.

90. Diuretics, including:
organomercurials such as Chlormerodrin, Meralluride, Mercamphamide, Mercaptomerin Sodium, Mercumallylic Acid, Mercumatilin Sodium, Mercurous Chloride and Mersalyl;
Pteridines such as Furterene and Triamterene;
Purines such as Acefylline, 7-Morpholinomethyltheophylline, Pamabrom, Protheobromine and Theobromine;
Steroids such as Canrenone, Oleandrin and Spironolactone;
Sulfonamide derivatives such as Acetazolmide, Ambuside, Azosemide, Bumetanide, Butazolamide, Chloraminophenamide, Clofenamide, Clopamide, Clorexolene, Diphenylmethane-4,4'-disulfonamide, Disulfamide, Ethoxzolamide, Furosemide, Indapamide, Mefruside, Methazolamide, Piretanide, Quinethazone, Torsemide, Tripamide and Xipamide;
Uracils such as Aminometradine and Amisometradine;
others such as Amanozine, Amiloride, Arbutin, Chlorazanil, Ethacrynic Acid, Etozolin, Hydracarbazine, Isosorbide, Mannitol, Metochalcone, Muzolimine, Perhexyline, Ticrynafen and Urea.

91. Dopamine receptor agonists such as Bromocriptine, Dopexamine, Fenoldopam, Ibopamine, Lisuride, Naxagolide and Pergolide.

92. Ectoparasiticides such as Amitraz, Benzyl Benzoate, Carbaryl, Crotamiton, DDT, Dixanthogen, Isobornyl Thiocyanoacetate—Technical, Lime Sulfurated Solution, LIndane, Malathion, Mercuric Oleate, Mesulphen and Sulphur—Pharmaceutical.

93. Enzymes, including:
Digestive enzymes such as a-Amylase (Swine Pancreas), Lipase, Pancrelipase, Pepsin and Rennin;
Mucolytic enzymes such as Lysozyme;
Penicillin inactivating enzymes such as Penicillinase; and
Proteolytic enzymes such as Collagenase, Chymopapain, Chymotrypsins, Papain and Trypsin.

94. Enzyme inducers (hepatic) such as Flumecinol.

95. Estrogens (non-steroidal) such as Benzestrol, Broparoestrol, Chlorotrianisene, Dienestrol, Diethylstilbestrol, Diethylstilbestrol Diproprionate, Dimestrol, Fosfestrol, Hexestrol, Methallenestril and Methestrol.

Estrogens such as Conjugated Estrogenic Hormones, Equilenin, Equilin, Esterified Estrogens, 17β-Estradiol, Estradiol Benzoate, 17β-Estradiol Valerate, Estradiol 17β-Cypionate, Estriol, Estrone, Estropipate, 17β-Ethinyl Estradiol and Mestranol 96. Gastric secretion inhibitors such as Enterogastrone and Octreotide.

97. Glucocorticoids such as 21-Acetoxyprefnenolone, Aalclometasone, Algestone, Amicinonide, Beclomethasone, Betamethasone, Budesonide, Chloroprednisone, Clobetasol, Blovetasone, Clocortolone, Cloprednol, Corticosterone, Cortisone, Cortivazol, Deflazacort, Desonide, Desoximetasone, Dexamethasone, Diflorasone, Diflucortolone, Difluprednate, Enoxolone, Fluazacort, Flucloronide, Flumehtasone, Flunisolide, Fluocinolone Acetonide, Fluocinonide, Fluocortin Butyl, Fluocortolone, Fluorometholone, Fluperolone Acetate, Fluprednidene Acetate, Fluprednisolone, Flurandrenolide, Formocortal, Halcinonide, Halometasone, Halopredone Acetate, Hydrocortamate, Hydrocortisone, Hydrocortisone Acetate, ydrocortisone Phosphate, Hydrocortisone 21-Sodium Succinate, Hydrocortisone Tebutate, Mazipredone, Medrysone, Meprednisone, Methyolprednisolone, Mometasone Furoate, Paramethasone, Prednicarbate, Prednisolone, Prednisolone 21-Diethylaminoacetate, Prednisone Sodium Phosphate, Prednisolone Sodium Succinate, Prednisolone Sodium 21-m-Sulfobenzoate, Prednisolone 21-Stearoylglycolate, Prednisolone Tebutate, Prednisolone 21-Trimethylacetate, Prednisone, Prednival, Prednylidene, Prednylidene 21-Diethylaminoacetate, Tixocortal, Triamcinolone, Triamcinolone Acetonide, Triamcinolone Benetonide and Triamcinolone Hexacetonide.

98. Gonad-Stimulating principles such as Buserelin, Clomiphene, Cyclofenil, Epimestrol, FSH, HCG and LH-RH.

99. Gonadotropic hormones such as LH and PMSG.

100. Growth hormone inhibitors such as Octreotide and Somatostatin.

101. Growth hormone releasing factors such as Semorelin.

102. Growth stimulants such as Somatotropin.

103. Hemolytic agents such as Phenylhydrazine and Phenylhydrazine Hydrochloride.

104. Heparin antagonists such as Hexadimethrine Bromide and Protamines.

105. Hepatoprotectants such as S-Adenosylmethionine, Betaine, Catechin, Citolone, Malotilate, Orazamide, Phosphorylcholine, Protoporphyrin IX, Silymarin-Group, Thiotic Acid and Tiopronin.

106. Immunomodulators such as Amiprilose, Bucillamine, Ditiocarb Sodium, Inosine Pranobex, Interferon-y, Interleukin-2, Lentinan, Muroctasin, Platonin, Procodazole, Tetramisole, Thymomodulin, Thymopentin and Ubenimex.

107. Immunosuppressants such as Azathioprine, Cyclosporins and Mizoribine.

108. Ion exchange resins such as Carbacrylic Resins, Cholestyramine Resin, Colestipol, Polidexide, Resodec and Sodium Polystyrene Sulfonate.

109. Lactation stimulating hormone such as Prolactin.

110. LH-RH agonists such as Buserelin, Goserelin, Goserelin Acetate, Leuprolide, Nafarelin, and Triptorelin.

111. Lipotropic agents such as N-Acetylmethionine, Choline Chloride, Choline Dehydrocholate, Choline Dihydrogen Citrate, Inositol, Lecithin and Methionine.

112. Lupus erythematosus suppressants such as Bismuth Sodium Triglycollamate, Bismuth Subsalicylate, Chloroquine and Hydroxychloroquine.

113. Mineralcorticoids such as Aldosterone, Deoxycorticosterone, Deoxycorticosterone Acetate and Fludrocortisone.

114. Miotic drugs such as Carbachol, Physostigmine, Pilocarpine and Pilocarpus.

115. Monoamine oxidase inhibitors such as Deprenyl, Iproclozide, Iproniazid, Isocarboxazid, Moclobemide, Octomoxin, Pargyline, Phenelzine, Phenoxypropazine, Pivalylbenzhydrazine, Prodipine, Toloxatone and Tranylcypromine.

116. Mucolytic agents such as Acetylcysteine, Bromhexine, Carbocysteine, Domiodol, Letosteine, Lysozyme, Mecysteine Hydrochloride, Mesna, Sobrerol, Stepronin, Tiopronin and Tyloxapol.

117. Muscle relaxants (skeletal) such as Afloqualone, Alcuronium, Atracurium Besylate, Baclofen, Benzoctamine, Benzoquinonium Chloride, C-Calebassine, Carisoprodol, Chlormezanone, Chlorphenesin Carbamate, Chlorproethazine, Chlozoxazone, Curare, Cyclarbamate, Cyclobenzaprine, Dantrolene, Decamethonium Bromide, Diazepam, Eperisone, Fazadinium Bromide, Flumetramide, Gallamine Triethiodide, Hexacarbacholine Bromide, Hexafluorenium Bromide, Idrocilamide, Lauexium Methyl Sulfate, Leptodactyline, Memantine, Mephenesin, Mephenoxalone, Metaxalone, Methocarbamol, Metocurine Iodide, Nimetazepam, Orphenadrine, Pancuronium Bromide, Phenprobamate, Phenyramidol, Pipecurium Bromide, Promoxolane, Quinine Sulfate, Styramate, Succinylcholine Bromide, Succinylcholine Chloride, Succinylcholine Iodine, Suxethonium Bromide, Tetrazepam, Thiocolchicoside, Tizanidine, Tolperisone, Tubocurarine Chloride, Vecuronium Bromide and Zoxolamine.

118. Narcotic antagonists such as Amiphenazole, Cyclazocine, Levallorphan, Nadide, Nalmfene, Nalorphine, Nalorphine Dinicotinate, Naloxone and Naltrexone.

119. Neuroprotective agents such as Dizocilpine.

120. Nootropic agents such as Aceglutamide, Acetylcarnitine, Aniracetam, Bifematlane, Exifone, Fipexide, Idebenone, Indeloxazine Hydrochloride, Nizofenone, Oxiracetam, Piracetam, Propentofylline, Pyritinol and Tacrine.

121. Ophthalmic agents such as 15-ketoprostaglandins.

122. Ovarian hormone such as Relaxin.

123. Oxytocic drugs such as Carboprost, Cargutocin, Deaminooxytocin, Ergonovine, Gemeprost, Methylergonovine, Oxytocin, Pituitary (Posterior), Prostaglandin $E_2$, Prostaglandin $F_{2a}$ and Sparteine.

124. Pepsin inhibitors such as Sodium Amylosulfate.

125. Peristaltic stimulants such as Cisapride.

126. Prolactin inhibitors such as Metergoline.

127. Prostaglandins and prostaglandin analogs such as Arbaprostil, Carboprost, Enprostil, Bemeprost, Limaprost, Misoprostol, Omoprostil, Prostacyclin, Prostaglandin $E_1$, Prostaglandin $E_2$, Prostagland in $F_{2a}$ Rioprostil, Rosaprostol, Sulprostone and Trimoprostil.

Progestational agents such as Chlormadinone and Chlormadinone Acetate, Demegestone, Desogestrel, Dimethisterone, Dydrogesterone, Ethinylestrenol, Ethisterone, Ethynodiol and Ethynodiol Diacetate, Gestodene, 17α-Hydroxyprogesterone, Hydroxygesterone Caproate, Medroxyprogesterone and Medroxyprogesterone Acetate, Megestrol Acetate, Melengestrol, Norethindrone and Norethidrone Acetate, Norethynodrel, Norgesterone, Norgestrel, 19-Norprogesterone, Progesterone, Promegestone and esters thereof. Free base forms of drugs which have a greater affinity for the acid (carboxyl) functional group in a carboxyl functional acrylic-based polymer are preferred in some applications.

128. Protease inhibitors such as Aprotinin, Camostat, Gabexate and Nafamostat.

129. Respiratory stimulants such as Almitrine, Bemegride, Carbon Dioxide, Cropropamide, Crotethamide, Dimefline, Dimorpholamine, Doxapram, Ethamivan, Fominoben, Lobeline, Mepixanox, Metamivam, Nikethamide, Picrotoxin, Pimeclone, Pyridofylline, Sodium Succinate and Tacrine.

130. Sclerosing agents such as Ethanolamine, Ethylamine, 2-Hexyldecanoic Acid, Polidocanol, Quinine Bisulfate, Quinine Urea Hydrochloride, Sodium Ricinoleate, Sodium Tetradecyl Sulfate and Tribenoside.

131. Sedatives and hypnotics, including:

Acyclic ureides such as Acecarbromal, Apronalide, Bomisovalum, Capuride, Carbromal and Ectylurea;

Alcohols such as Chlorhexadol, Ethchlorvynol, Meparfynol, 4-Methyl-5-thiazoleethanol, tert-Pentyl Alcohol and 2,2,2-Trichloroethanol;

Amides such as Butoctamide, Diethylbromoacetamide, Ibrotamide, Isovaleryl Diethylamide, Niaprazine, Tricetamide, Trimetozine, Zolpidem and Zopiclone;

Barbituric acid derivatives such as Allobarbital, Amobarbital, Aprobarbital, Barbital, Brallabarbital, Butabarbital Sodium, Butalbital, Butallylonal, Butethal, Carbubarb, Cyclobarbital, Cyclopentobarbital, Enallylpropymal, 5-Ethyl-5-(1-piperidyl)barbituric Acid, 5-Furfuryl-5-isopropylbarbituric Acid, Heptabarbital, Hexethal Sodium, Hexobarbital, Mephobarbital, Methitural, Narcobarbital, Nealbarbital, Pentobarbital Sodium, Phenallymal, Phenobarbital, Phenobarbital Sodium, Phenylmethylbarbituric Acid, Probarbital, Propallylonal, Proxibarbal, Reposal, Secobarbital Sodium, Talbutal, Tetrabarbital, Vinbarbital Sodium and Vinylbital;

Benzodiazepine derivatives such as Brotizolam, Doxefazepam, Estazolam, Flunitrazepam, Flurazepam, Haloxazolam, Loprazolam, Lormetazepam, Nitrazepam, Quazepam, Temazepam and Triazolam;

Bromides such as Ammonium Bromide, Calcium Bromide, Calcium Bromolactobionate, Lithium Bromide, Magnesium Bromide, Potassium Bromide and Sodium Bromide;

Carbamates such as Amyl Carbamate—Tertiary, Ethinamate, Hexaprpymate, Meparfynol Carbamate, Novonal and Tricholorourethan;

Chloral derivatives such as Carbocloral, Chloral Betaine, Chloral Formamide, Chloral Hydrate, Chloralantipyrine, Dichloralphenazone, Pentaerythritol Chloral and Triclofos;

Piperidinediones such as Glutehimide, Methyprylon, Piperidione, Pyrithyldione, Taglutimide and Thalidomide;

Quinazolone derivatives such as Etaqualone, Mecloqualone and Methaqualone; and others such as Acetal, Acetophenone, Aldol, Ammonium Valerate, Amphenidone, d-Bornyl a-Bromoisovalerate, d-Bornyl Isovalerate, Bromoform, Calcium 2-Ethylbutanoate, Carfinate, a-Chlorolose, Clomethiazole, Cypripedium, Doxylamine, Etodroxizine, Etomidate, Fenadiazole, Homofenazine, Hydrobromic Acid, Mecloxamine, Menthyl Valerate, Opium, Paraldehyde, Perlapine, Propiomazine, Rilmazafone, Sodium Oxybate, Sulfonethylmethane and Sulfonmethane.

132. Thrombolytic agents such as APSAC, Plasmin, Pro-Urokinase, Streptokinase, Tissue Plasminogen Activator and Urokinase.

133. Thyrotropic hormones such as TRH and TSH.

134. Uricosurics such as Benzbromarone, Ethebenecid, Orotic Acid, Oxycinchophen, Probenecid, Sulfinpyrazone, Ticrynafen and Zoxazolamine.

135. Vasodilators (cerebral) such as Bencyclane, Cinnarizine, Citicoline, Cyclandelate, Ciclonicate, Diisopropylamine Dichloractetate, Ebumamonine, Fenoxedil, Flunarizine, Ibudilast, Ifenprodil, Nafronyl, Nicametate, Nicergoline, Nimodipine, Papaverine, Pentifylline, Tinofedrine, Vincamine, Vinpocetine and Viquidil.

136. Vasodilators (coronary) such as Amotriphene, Bendazol, Benfurodil Hemisuccinate, Benziodarone, Chloacizine, Chromonar, Clobenfurol, Clonitrate, Dilazep, Dipyridamole, proprenilamine, Efloxate, Erythritol, Erythrityl Tetranitrate, Etafenone, Fendiline, Floredil, Ganglefene, Hexestrol Bis(β-diethylaminoethyl ether), Hexobendine, Itramin Tosylate, Khellin, Lidoflazine, Mannitol Hexanitrate, Medibazine, Nicorandil, Nitroglycerin, Pentaerythritol Tetranitrate, Pentrinitrol, Perhexyline, Pimethylline, Prenylamine, Propatyl Nitrate, Pyridofylline, Trapidil, Tricromyl, Trimetazidine, Trolnitrate Phosphate and Visnadine.

137. Vasodilators (peripheral) such as Aluminum Nicotinate, Bamethan, Bencyclane, Betahistine, Bradykinin, Brovincamine, Bufoniode, Buflomedil, Butalamine, Cetiedil, Ciclonicate, Cinepazide, Cinnarizine, Cyclandelate, Diisopropylamine Dichloracetate, Eledoisin, Fenoxidil, Flunarisine, Heronicate, Ifenprodil, Inositol Niacinate, Isoxsuprine, Kallidin, Kallikrein, Moxisylyte, Nafronyl, Nicametate, Nicergoline, Nicofuranose, Nicotinyl Alcohol, Nylidrin, Pentifylline, Pentoxifylline, Piribedil, Protaglandin $E_1$, Suloctidil and Xanthinal Niacinate.

138. Vasoprotectants such as Benzarone, Bioflavonoids, Chromocarb, Clobeoside, Diosmin, Dobesilate Calcium, Escin, Rolescutol, Leucocyanidin, Metescufylline, Quercetin, Rutin and Troxerutin.

139. Vitamins, vitamin sources, and vitamin extracts such as Vitamins A, B, C, D, E, and K and derivatives thereof, Calciferols, Glycyrrhiza and Mecobalamin.

140. Vulnerary agents such as Acetylcysteine, Allantoin, Asiaticoside, Cadexomer Iodine, Chitin, Dextranomer and Oxaceprol.

141. Anticoagulants such as heparin.

142. Miscellaneous such as Erythropoietin (Hematinic), Filgrastim, Finasteride (Benign Prostate Hypertrophy), Interferon Beta 1-Alpha (Multiple Sclerosis) and Tretinonin (Urinary Incontinence).

Particular drugs that are usable in the present invention include low molecular weight drugs. Any drug which is liquid at or about room temperature can be used according to the present invention. As used herein, the term "low molecular weight" is defined to include any drug and its equivalent forms that has a melting point such that it exists as a liquid at or about room temperatures. This term encompasses low molecular weight drugs having a molecular weight of less than about 300 daltons. A drug which is of low molecular weight and liquid at or about room temperatures is generally in its free-base or free-acid form, and, as such, is encompassed by this term. Drugs usable in practicing the invention include amphetamine, d-amphetamine, l-amphetamine, d,l-amphetamine, methaphetamine, prilocaine, benzocaine, butacaine, butamben, butanilicaine, corticaine, lidocaine, memantine, pilocarpine, cyclobenzaprine, paroxetine, fluoxetine, duloxetine, imipramine, decipramine, doxeprin, nortriptylene, protriptylene, bupropion, azelastine, chlorphenamine, bisoprolol, pheniramine, alprazolam, captopril, clonidine, clonazepam, enalapril, ramipril, haloperidol, ketoprofen, loratadine, methimazole (anti-hyperthyroid), methylphenidate, methyl testosterone, nicotine, nitroglycerin, pramipexole, ropinirole, hydromorphone, scopolamine, testosterone, methamphetamine, frovatriptan and phentermine. For desired therapeutic effect, it may be desirable certain drugs, such as methylphenidate, d-amphetamine, methamphetamine and phentermine, be used in their base form.

The amount of drug to be incorporated in the composition varies depending on the particular drug, the desired therapeutic effect, and the time span for which the device is to provide therapy. For most drugs, the passage of the drugs through the skin will be the rate-limiting step in delivery. Thus, the amount of drug and the rate of release is typically selected so as to provide transdermal delivery characterized by a zero order time dependency for a prolonged period of time. The minimum amount of drug in the system is selected based on the amount of drug which passes through the skin in the time span for which the device is to provide therapy. Normally, the amount of drug in the system can vary from about 0.1% to about 50%. However, the composition of this invention is particularly useful for drugs which are used in relatively low concentrations, especially 0.3% to 30% of the total composition, more preferably from about 0.5% to about 15% of the total composition, most preferably from about 1% to about 10% of the total composition.

One preferred drug in clonidine. Clonidine is an anti-sympathicotonic agent having an imidazoline structure. It has affinity for $\alpha_1$-adrenoceptors and—more strongly—for pre- and post-synaptic $\alpha_2$-adrenoceptors and lowers peripheral sympathetic tone. It is believed that clonidine lowers blood pressure by decreasing cardiac output and—in the case of prolonged medication—by reducing peripheral vascular resistance. At the same time, it is believed that clonidine reduces the release of renin with a decrease in angiotensin II in the blood plasma, with aldosterone being released from the adrenal cortex.

Clonidine may be used, for example, in treating the following indications: hypertension, migraine, anxiety states, hyperkinetic behavioural disorders, withdrawal symptoms in alcohol or drug withdrawal, and menopausal symptoms.

Clonidine hydrochloride exists in the form of a mesomeric component. The chemical name is 2-(2,6-dichlorophenylamino)-2-imidazoline hydrochloride. Clonidine has the following molecular formula: $C_9H_9Cl_2N_3HCl$, and a molecular weight of 266.56.

As used herein, the term "supersaturated" used in reference to the drug means that the amount of drug present is in excess of its solubility or dispersability in a multiple polymer adhesive system.

Referring to FIG. 1, the most preferred embodiment of the invention, transdermal drug delivery system 10 comprises a carrier composition layer 12 incorporating the active agent. Surface 14 of the adhesive carrier composition layer 12 is affixed to release liner 15 to protect the carrier composition layer prior to use but which is removed upon topical application of the carrier composition layer to the skin or mucosa of the user. A non-drug containing backing layer 18 is affixed to the other surface 20 of the carrier composition layer 12. As discussed in more detail below, backing layer 18 may be made of any suitable material to tailor delivery of the active agent from the carrier composition layer 12 to the skin or mucosa of the user. The backing layer 18 may be processed separately from carrier layer 12 or may be processed together with the carrier composition layer 12.

Carrier composition layer 12 can comprise any polymer or adhesive generally known in the art for formulating a drug carrier composition, and include all of the non-toxic natural and synthetic polymers known or suitable for use in transdermal systems including solvent-based, hot melt and grafted adhesives, and may be used alone or in combinations, mixtures or blends. Examples include acrylic-based polymer(s), silicone-based polymer(s), rubbers, gums, polyisobutylenes, polyvinylethers, polyurethanes, styrene block copolymers, styrene/butadiene polymers, polyether block amide copolymers, ethylene/vinyl acetate copolymers, and vinyl acetate based adhesives, and bioadhesives as set forth in U.S. Pat. No. 6,562,363 which is expressly incorporated by reference in its entirety.

The term "silicone-based" polymer is intended to be used interchangeably with the terms siloxane, polysiloxane, and silicones as used herein and as known in the art. The silicone-based polymer may also be a pressure-sensitive adhesive, with a polysiloxane adhesive prepared by cross-linking an elastomer, typically a high molecular weight polydiorganosiloxane, with a resin, to produce a three-dimensional siloxane structure, via a condensation reaction in an appropriate organic solvent. The ratio of resin to elastomer is a critical factor that can be adjusted in order to modify the physical properties of polysiloxane adhesives. Sobieski, et al., "Silicone Pressure Sensitive Adhesives," Handbook of Pressure-Sensitive Adhesive Technology. 2nd ed., pp. 508-517 (D. Satas, ed.), Van Nostrand Reinhold, N.Y. (1989). Further details and examples of silicone pressure-sensitive adhesives which are useful in the practice of this invention are described in the following U.S. Pat. Nos. 4,591,622; 4,584,355; 4,585, 836; and 4,655,767, all expressly incorporated by reference in their entireties. Suitable silicone pressure-sensitive adhesives are commercially available and include the silicone adhesives sold under the trademarks BIO-PSA® by Dow Corning Corporation, Medical Products, Midland, Mich. (such as -2685, -3027, -3122, -4101, -4102, -4203, -4301, -4302, -4303, -4401-4403, -4501, -4503, -4602, -4603 and -4919). Capped silicones with high resin content are preferred.

In the practice of the preferred embodiments of the invention, the carrier composition layer 12 includes an acrylic-based polymer. The acrylic-based polymer can be any of the homopolymers, copolymers, terpolymers, and the like of various acrylic acids. In such preferred embodiments, the acrylic-based polymer constitutes from about 2% to about 95% of the total dry weight of the of the carrier composition, and preferably from about 2% to about 90%, and more preferably from about 2% to about 85% of the carrier composition, wherein the amount of the acrylic-based polymer is dependent on the amount and type of drug used.

The acrylic-based polymers usable in the invention are polymers of one or more monomers of acrylic acids and other copolymerizable monomers. The acrylate polymers also include copolymers of alkyl acrylates and/or methacrylates and/or copolymerizable secondary monomers or monomers with functional groups. By varying the amount of each type of monomer added, the cohesive properties of the resulting acrylate polymer can be changed as is known in the art. In general, the acrylate polymer is composed of at least 50% by weight of an acrylate or alkyl acrylate monomer, from 0 to 20% of a functional monomer copolymerizable with the acrylate, and from 0 to 40% of other monomers.

Acrylate monomers which can be used include acrylic acid, methacrylic acid, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate.

Functional monomers, copolymerizable with the above alkyl acrylates or methacrylates, which can be used include acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate and methoxyethyl methacrylate.

Suitable acrylic-based polymers may also be a pressure-sensitive adhesive which are commercially available and include the acrylic-based adhesives sold under the trademarks Duro-Tak® by National Starch and Chemical Corporation, Bridgewater, N.J. (such as 87-2287, -4098, -2852, -2196, -2296, -2194, -2516, -2070, -2353, -2154, -2510, -9085-9088 and 73-9301). Other suitable acrylic-based adhesives include those sold by Monsanto; St. Louis, Mo., under the trademarks Gelva® Multipolymer Solution (such as 2480, 788, 737, 263, 1430, 1753, 1151, 2450, and 2495 and Eudragit® sold by Roehm Pharma GmbH, Darmstadt, Federal Republic of Germany.

The carrier composition may comprise blends of acrylic-based polymers, silicone-based polymers and rubbers based upon their differing solubility parameters, alone or in combination with other polymers, for example polyvinylpyrrolidone, as more fully described in U.S. Pat. Nos. 5,474,783; 5,656,286; 5,958,446; 6,024,976; 6,221,383; and 6,235,306; which are incorporated herein in their entirety. The amount of each polymer is selected to adjust the saturation concentration of the drug in the multiple polymer system, and to result in the desired rate of delivery of the drug from the system and through the skin or mucosa.

Combinations of acrylic-based polymers based on their functional groups is also contemplated. Acrylic-based polymers having functional groups are copolymers or terpolymers which contain in addition to nonfunctional monomer units, further monomer units having free functional groups. The monomers can be monofunctional or polyfunctional. These functional groups include carboxyl groups, hydroxy groups, amino groups, amido groups, epoxy groups, etc. Preferred functional groups are carboxyl groups and hydroxy groups. Preferred carboxyl functional monomers include acrylic acid, methacrylic acid, itaconic acid, maleic acid, and crotonic acid. Preferred hydroxy functional monomers include 2-hydroxyethyl methacrylate, 2-hydroxyethyl acrylate, hydroxymethyl acrylate, hydroxymethyl methacrylate, hydroxyethyl acrylate, hydroxyethyl methacrylate, hydroxypropyl acrylate, hydroxypropyl methacrylate, hydroxybutyl acrylate, hydroxybutyl methacrylate, hydroxyamyl acrylate, hydroxyamyl methacrylate, hydroxyhexyl acrylate, hydroxyhexyl methacrylate. Non-functional acrylic-based polymers can include any acrylic based polymer having no or substantially no free functional groups. The acrylic based polymer can include homopolymers, copolymers and terpolymers. The monomers used to produce the polymers can include alkyl acrylic or methacrylic esters such as methyl methacrylate, ethyl acrylate, propyl acrylate, amyl acrylate, butyl acrylate, 2-ethylbutyl acrylate, hexyl acrylate, heptyl acrylate, octyl acrylate, nonyl acrylate, 2-ethylhexyl acrylate, decyl acrylate, dodecyl acrylate, tridecyl acrylate, glycidyl acrylate and the corresponding methacrylic esters.

Both the acrylic-based polymer having substantially no functional groups and acrylic-based polymers having functional groups can optionally include further modifying monomers. These modifying monomers can include any conceivable monomer that is capable of undergoing vinyl polymerization. For example, the incorporation of styrene monomers can be used to increase the glass transition temperature and are sometimes used to improve the cohesive strength. The copolymerization of vinyl acetate monomers with acrylic esters are also used to form acrylic-based polymers. Ethylene can also be copolymerized with acrylic esters and vinyl acetate to give suitable acrylic-based polymers.

For example, a composition will require less of a functional acrylic that contains 20% by weight of functional groups as opposed to one that contains 0.5% by weight of functional groups to achieve the same effect required for solubility and flux. Broadly speaking, the amount of functional acrylic is generally within the range of about 1 to 99 weight % and preferably 5 to 95 weight %, more preferably 20 to 75 weight %, even more, preferably 30 to 65 weight %, based on the total polymer content of the transdermal composition. The amount of non-functional acrylic or acrylic with a functional group which does not have as great of an affinity for the drug, is within the range of about 99 to 1 weight %, preferably 95 to 5 weight %, more preferably 75 to 20 weight % and even more preferably 30 to 65 weight %, based on the total polymer content of the composition.

Further details and examples of acrylic-based adhesives, functional monomers, and polymers which have no functional groups and which are suitable in the practice of the invention are described in Satas, "Acrylic Adhesives,"Handbook of Pressure-Sensitive Adhesive Technology, 2nd ed., pp. 396-456 (D. Satas, ed.), Van Nostrand Reinhold, N.Y. (1989); "Acrylic and Methacrylic Ester Polymers," Polymer Science and Engineering, Vol. 1, 2nd ed., pp 234-268, John Wiley & Sons, (1984); U.S. Pat. No. 4,390,520; and U.S. Pat. No. 4,994,267 all of which are expressly incorporated by reference in their entireties.

The required proportions of acrylic-based or other polymers used are generally dependant on the specific drug, its desired delivery rate and the desired duration of drug delivery. In general, proportions of acrylic-based polymers also depend on the content of the functional monomer units in the functional acrylic.

When the drug carrier composition is intended to function as the face layer, that is the layer 14 that comes in contact with the topical site of application as depicted in FIG. 1, it is preferable that the carrier composition comprise a pressure-sensitive adhesive or bioadhesive.

The backing layer 18 comprises at least one layer, the primary layer having a high water vapor transmission rate and a moderate to low gas transmission rate. Thus, the backing has a water vapor transmission rate about equal to or in excess of that of ethylene vinyl alcohol copolymer (EVOH) and a gas transmission rate about equal to or less than EVOH, in which the EVOH is of about 0.2 to 3 mil thickness. The backing can comprise additional polymeric layers, for example, a second layer having a high water vapor transmission rate, as well as additional layers. The additional layers can be placed on one or both sides of the first layer. Suitable backings are disclosed in U.S. Pat. No. 4,994,278 which is herein incorporated by reference in its entirety.

Basically, the backing material is constructed of a barrier polymer or resin or other permeable material. The term "barrier" is used here in reference to a material's resistance to absorption, diffusion, and desorption of gases, moisture and other chemicals. By the use of certain barrier materials, a film can be made selectively permeable to water or other liquid vapor rather than gas or vice versa. The backing layer 18 has a thickness from about 0.2 mm to about 3 mm.

The permeability to gas and moisture vapor is known or can be computed using standardized tests. A comparison of different plastics is found in "Barrier Resins Key New Package Development", Plastics Packaging, July/August 1988, pp. 17-21.

TABLE 1

Comparison of Barrier Properties for Commercial polymers

| Material | Oxygen Transmission Rate 25° C., 65/RH (cc-mil/100 in$^2$ - 24 hours) | Moisture Vapor Transmission Rate, 40° C., 90/RH (cc-mil/100 in$^2$ 2 hours) |
|---|---|---|
| Ethylene vinyl alcohol | 0.05 to 0.18 | 1.4 to 5.4 |
| Polyvinylidene chloride | 0.15 to 0.90 | 0.1 to 0.2 |
| Acrylonitrile | 0.80 | 5.0 |
| Amorphous nylon | 0.74 to 2.0 | |
| Oriented polyester terephthalate | 2.60 | 1.2 |
| Oriented nylon | 2.10 | 9.0 |
| Rigid polyvinyl chloride | 14.0 | 3.0 |
| Low density polyethylene | 420 | 1.0 to 1.5 |
| High density polyethylene | 150 | 0.4 |
| Polypropylene | 150 | 0.69 |
| Polystyrene | 350 | 7 to 10 |

In the above table, oxygen transmission rate is expressed in cubic centimeters of oxygen of 1 mil film per 100 square inches surface area per 24 hours at 65% relative humidity (RH) and 25° Celsius (° C.) and moisture vapor transmission rate is expressed in cubic centimeters per 100 square inches of surface area of 1 mil film per 24 hours at 40 degrees Celsius (° C.) and 90% relative humidity Additional moisture vapor transmission rates are:

TABLE 2

| | Moisture Vapor Transmission Rate (40° C./90% R.H.) | |
|---|---|---|
| | g 30 microns/m$^2$/ 24 Hrs | g. mil/100 in$^2$/ 24 Hrs |
| Biaxially Oriented Polypropylene | 5 | 0.38 |
| High Density Polyethylene | 5 | 0.38 |
| Polypropylene | 9 | 0.69 |
| Low Density Polyethylene | 15 | 1.14 |
| Biaxially Oriented Polyester Terephthalate | 15 | 1.2 |
| Rigid Polyvinyl Chloride | 40 | 3.1 |
| Polystyrene | 112 | 8.5 |
| Biaxially Oriented Nylon 6 | 134 | 10.0 |
| Polycarbonate | 14.5 | 1.1 |
| EVAL EP-F | 50 | 3.8 |
| EVAL EP-H | 28 | 2.1 |
| EVAL EP-K | 28 | 2.1 |
| EVAL EP-E | 19 | 1.4 |
| EVAL EP-G | 19 | 1.4 |
| Saran 5253 PVC | 3 | 0.22 |
| Barex 210 Nitrile | 80 | 6.1 |

A suitable backing layer 18 according to the present invention should:

1. Maintain its physical and chemical integrity in the environment of use;
2. Provide mechanical support for the other laminae forming a laminate carrier;
3. Be substantially impermeable to the pharmacological agent;
4. Be selectively permeable to the passage of internal water vapor; and
5. Be substantially impermeable to gases to water or moisture but permeable to water vapor.

The molecular weight of the polymers selected for the backing are such that the backing has the foregoing characteristics and the layers, the indicated water vapor and oxygen transmission rates.

Suitable polymeric materials for the transdermal backing include acrylonitrile, cellulose acetate, polycarbonate, ethylene vinyl acetate, ethylene methyl acrylate, polyester, polyethylene, polypropylene, polystyrene, polyurethane, polyvinyl alcohol, ethylene vinyl alcohol, polyamides, polyvinylidene chloride and polyvinyl chloride. Some polymers increase barrier properties by orienting the polymer chains in one or two directions.

The backing material of this invention comprises at least one, and can contain two or more natural or synthetic polymeric layers. At least one layer of the backing is composed of a polymer which is compatible with the drug chosen and with which the drug is compatible, is flexible, and has a water vapor transmission rate equal to or greater than EVOH of 0.2 to 3 mil thickness, namely a rate equal to or in excess of about 2 to 4 grams/100 in$^2$ per 24 hours, at 40° C. and 90% RH and more preferably 6 grams and an oxygen transmission rate equal to or less than EVOH of 0.2 to 3 mil thickness, namely of less than 0.01 to 0.1 cubic centimeters per 100 square inch when measured over 24 hours at one atmosphere pressure, 20° C. and 65% relative humidity.

The backing can also have a second or additional layers composed of a polymer which is compatible with the drug chosen and with which the drug is compatible, is flexible, and has a water vapor transmission rate in excess of that of EVOH of 0.2 to 3 mil thickness, namely in excess of about 2 to 4 grams per 100 square inches per 24 hours, at 40° C. and 90% relative humidity and preferably in excess of 6 grams.

The water vapor transmission rate of a given polymer is a function of the polymer and thus varies with the average molecular weight, configuration and orientation, chain length, nature of repeating units, the degree of crosslinking, the degree of crystallinity, the nature and extent of the monomer and the like, as well as time, temperature, relative humidity and thickness of the film. The rate thus varies, not only from polymer to polymer, but to different types of a specific polymer.

The preferred polymers for the additional layers are those having the greater water vapor transmission rate, thus the preferred polymers are cellulose acetate, nylon, polycarbonate, acrylonitrile, polystyrene, polyurethane and polyvinyl alcohol, or copolymers or multipolymers of these plastics with additional monomers. Polyurethane is an especially preferred material for the secondary layer.

Thus, the breathable backing of this invention comprises at least one layer of a substance having a high water vapor transmission rate and a low gas transmission rate. These physical properties can be found in the highly polar polymers, such as those containing hydroxyl groups such as polyvinyl alcohol, and ethylene vinyl alcohol, see e.g., Barrier Polymers article, 1977, p. 156. More particularly, ethylene vinyl alcohol copolymer (EVOH) has a particularly low gas transmission rate.

The backing material can consist of a single layer having the indicated high water vapor transmission rate and low gas transmission rate. In addition, a single or multi-layered material can be used on one or both sides of the primary layer. These secondary layers need only have the high water vapor transmission rate and can be used to minimize potential degradation of the primary layer by the presence of air and moisture. The substances selected for additional polymeric layers can be the same or of different polymers.

In general, the additional layers have a moisture vapor transmission rate (MVTR) in excess of that of EVOH of 0.2 to 3 mil thickness, namely in excess of about 2 to 4 grams per 100 square inches at 40° C., 90% relative humidity over 24 hours, and more preferably in excess of about 6 grams per 100 square inch and more preferably in excess of 9 grams per 100 square inch.

The backing can be prepared by any of the methods used to join plastics in a film, including lamination or coextrusion. In the case of lamination, various means known in the art can be utilized to cause the layers to adhere.

Typically, each layer of the laminate is approximately 5 to 100 microns, and preferably 12 to 75 microns in thickness.

The preferred backing material for use in this invention is a layer of ethylene vinyl alcohol copolymer laminated or coextruded with polyurethane. An especially preferred backing material for use in this invention is one in which the polyurethane film is that available from JP Stevens, East Hampton, Mass. The preferred ethylene vinyl alcohol copolymer is the polymer sold under the trademark "EVAL" item EF-F, available from EVAL Company of America, Lisle, Ill.

The layers are juxtaposed face to face, and are bonded to each other. They are sufficiently flexible to be able to adapt to the contour of the skin and movements therein.

It is known that the mole percent ethylene in an ethylene vinyl alcohol copolymer affects not only the oxygen transmission rate of the copolymer, but the sensitivity of that oxygen transmission rate to relative humidity. Thus, the lower the percentage of ethylene in ethylene vinyl alcohol copolymer, the lower the oxygen transmission rate. Thus, it has been reported that a 1.0 mil ethylene vinyl alcohol copolymer containing 29 mole percent ethylene has an oxygen transmission rate of less than 0.02 at 0% relative humidity and 68° F., and approximately 0.05 at 80% relative humidity. On the other hand, under the same conditions of relative humidity and temperature, ethylene vinyl alcohol copolymer containing 38 mole percent and 44 mole percent of ethylene has an oxygen transmission rate of about 0.06 to 0.07 at 0% relative humidity, rising to approximately 0.2% at 80% relative humidity. In contrast, a 1.0 mil nylon film has an oxygen transmission rate of just above 2 at relative humidities ranging from 0% to in excess of 80% at 73° F. Similarly, the coextrusion of an ethylene vinyl alcohol copolymer and nylon tends to lower the oxygen transmission rate through a wide range of relative humidities, as compared with the non-coextruded ethylene vinyl alcohol copolymer.

The backing layer 18 according to the present invention has a moisture vapor transmission rate of from 0 to about 1500 g/m$^2$/24 hrs, preferably about 0.5 to about 1000 g/m$^2$/24 hrs, still more preferably from about 1.5 to about 500 g/m$^2$/24 hrs, still more preferably from about 3 to about 250 g/m$^2$/24 hrs, most preferably from about 10 to about 100 g/m$^2$/24 hrs.

In general, therapeutic amounts of drug can be delivered from the transdermal drug delivery system containing about 0.1% to about 50% by weight of drug. However, the transdermal drug delivery system of this invention is particularly useful for drugs which are used in relatively low concentrations, especially 0.3% to 30% of the total transdermal drug delivery system, more preferably from about 0.5% to about 15% of the total transdermal drug delivery system, most preferably from about 1% to about 10% of the total transdermal drug delivery system.

The polymeric backing layer can be prepared to selectively control the desired delivery rate, onset and profile for the drug by varying the moisture vapor transmission rate of the backing layer. As demonstrated in the examples, employing a backing layer with a lower moisture vapor transmission rate, the flux of the drug increased. When the moisture vapor transmission rate was increased, the flux of the drug decreased. Thus, it is believed that by varying the moisture vapor transmission rate, the delivery rate of the drug from the transdermal device can be tailored.

While one or more acrylic-based adhesives are preferred for use as the non-drug loaded coating, other polymers, alone or in combination, may be used provided such polymers have the ability to (a) incorporate and hold drug from the drug-loaded carrier composition after manufacture, (b) maintain contact/adhesion to both the carrier composition and either the backing film/layer or the release liner, preferably without the use of additional adhesives, (c) not degrade or interfere with stability of the drug, and (d) release or deliver the drug to the skin or mucosa after topical application of the transdermal system.

In certain embodiments of the invention, an enhancer can be incorporated into either the carrier composition or the polymeric coating, or both. The term "enhancers" as used herein refers to substances used to increase permeability and/or accelerate the delivery of an active agent through the skin or mucosa, and include monhydric alcohols such as ethyl, isopropyl, butyl and benzyl alcohols; or dihydric alcohols such as ethylene glycol, diethylene glycol, or propylene glycol, dipropylene glycol and trimethylene glycol; or polyhydric alcohols such as glycerin, sorbitol and polyethylene glycol, which enhance drug solubility; polyethylene glycol ethers of aliphatic alcohols (such as cetyl, lauryl, oleyl and stearly) including polyoxyethylene (4) lauryl ether, polyoxyethylene (2) oleyl ether and polyoxyethylene (10) oleyl ether commercially available under the trademark BRIJ® 30, 93 and 97 from ICI Americas, Inc., and BRIJ® 35, 52, 56, 58, 72, 76, 78, 92, 96, 700 and 721; vegetable, animal and fish fats and oils such as cotton seed, corn, safflower, olive and castor oils, squalene, and lanolin; fatty acid esters such as propyl oleate, decyl oleate, isopropyl palmitate, glycol palmitate, glycol laurate, dodecyl myristate, isopropyl myristate and glycol stearate which enhance drug diffusibility; fatty acid alcohols such as oleyl alcohol and its derivatives; fatty acid amides such as oleamide and its derivatives; urea, and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered and esters of sorbitol and sorbitol anhydride such as polysorbate 20 commercially available under the trademark Tween® 20 from ICI Americas, Inc., as well as other polysorbates such as 21, 40, 60, 61, 65, 80, 81, and 85. Other suitable enhancers include oleic and linoleic acids, triacetin, ascorbic acid, panthenol, butylated hydroxytoluene, tocopherol, tocopherol acetate, tocopheryl linoleate. If enhancers are incorporated into the transdermal system, the amount typically ranges up to about 30%, and preferably from about 0.1% to about 15%, by weight based on the dry weight of the total carrier composition.

In addition to enhancers, there may also be incorporated various pharmaceutically acceptable additives and excipients available to those skilled in the art. These additives include tackifying agents such as aliphatic hydrocarbons, mixed aliphatic and aromatic hydrocarbons, aromatic hydrocarbons, substituted aromatic hydrocarbons, hydrogenated esters, polyterpenes, silicone fluid, mineral oil and hydrogenated wood rosins. Additional additives include binders such as lecithin which "bind" the other ingredients, or rheological agents (thickeners) containing silicone such as fumed silica, reagent grade sand, precipitated silica, amorphous silica, colloidal silicon dioxide, fused silica, silica gel, quartz and particulate siliceous materials commercially available as Syloid®, Cabosil®, Aerosil®, and Whitelite®, for purposes of enhancing the uniform consistency or continuous phase of the composition or coating. Other additives and excipients include diluents, stabilizers, fillers, clays, buffering agents, biocides, humectants, anti-irritants, antioxidants, preservatives, plasticizing agents, cross-linking agents, flavoring agents, colorants, pigments and the like. Such substances can be present in any amount sufficient to impart the desired properties to the composition or coating. Such additives or excipients are typically used in amounts up to 25%, and preferably from about 0.1% to about 10%, by weight based on the dry weight of the total carrier composition.

Transdermal system 10 further employs release liners 15 or removable/peelable covers and backings to protect and/or anchor the system or its components during manufacturing as described herein, or thereafter, and to enable handling and transportation.

The release liner is typically impermeable and occlusive, and must be compatible with the particular polymers or active agents so as not to interfere with the composition's ultimate application and therapeutic effect. Some suitable materials that can be used, singularly, in combination, as laminates, films, or as coextrusion, to form the release liner are well known in the art. When the release liner is composed of a material which typically does not readily release (i.e., is not easily removed or separated from the coating or composition to which it is affixed), for example paper, a releasable material such as a silicone, Teflon®, or the like may be applied to the surface by any conventional means. Preferred release liners are films commercially available from DuPont, Wilmington, Del., under the trademarks Mylar®, and fluoropolymer (silicone) coated films commercially available from Rexam Release, Oak Brook, Ill. under the trademarks FL2000® and MRL2000®, and from 3M Corporation, St. Paul, Minn. Sold under the trademarks ScotchPak® such as 1022.

The backing layer 18 may generally have a thickness in the range of 0.2 to 3 mm. The backing layer 18 may be pigmented, for example colored to either match with or conversely easily distinguish from the site of application, and/or contain printing, labeling and other means of identification and/or traceability of the transdermal unit or system itself. The backing layer 18 may further be made opaque or substantially opaque (i.e., preventing light or certain energy wavelengths from penetrating or passing through), such as by metallization, fillers, inks, dyes and the like, for purposes of protecting photosensitive active agents from degradation and/or preventing photoallergic reactions or irritations on the subject.

An exemplary general method of preparing transdermal system 10 is as follows:

An exemplary general method for the preparation of a preferred embodiment is as follows:

1. Appropriate amounts of pressure sensitivadhesive polymer, solvent(s), enhancer(s), and organic solvent(s) (for example toluene) are combined and thoroughly mixed together in a vessel.

2. The drug is then added to the mixture and agitation is carried out until the drug is uniformly mixed in.

3. The formulation is then transferred to a coating operation where it is coated onto a protective release liner at a controlled specified thickness. The coated product is then passed through an oven in order to drive off all volatile processing solvents.

4. The dried product on the release liner is then joined to the backing material and wound into rolls for storage.

5. Thereafter, desired size and shape delivery systems 10 are prepared by die-cutting or the like, from the rolled laminate and then packaged.

In certain other preferred embodiments, a non-woven drug permeable film/layer, such as a polyester film, may be interdisposed, such as pressure lamination, for structural support or ease of manufacturing (i.e., has no effect on controlling drug permeation or delivery) between the non-drug loaded coating and the drug-loaded carrier composition.

The order of the processing steps, the amount of the ingredients, and the amount and time of agitation or mixing may be important process variables which will depend on the specific polymers, active agents, solvents or co-solvents, enhancers and additives and excipients used in the transdermal system. These factors can be adjusted by those skilled in the art, while keeping in mind the objects of achieving the interaction between the drug carrier composition and the non-drug loaded coating. It is believed that a number of other methods, for example, other methods of coating that are well-known in the art, such as Mayer rod, gravure, knife-over roll, extrusion, casting, calendaring and molding, or changing the order of certain steps, can be carried out and will also give desirable results.

The weight per unit area of the dried contact adhesive layer (matrix) is usually in the range of from about 1 mg/cm$^2$ to about 20 mg/cm$^2$, and more preferably in the range of from about 2.5 mg/cm$^2$ to about 15 mg/cm$^2$. The delivery rate is in the range of from about 0.01 mg to about 100 mg of active agent per day, and more preferably in the range of from about 0.1 mg to about 50 mg per day.

Generally, the amount of drug sufficient to deliver a therapeutically effective amount of the active agent at a substantially zero-order kinetic rate of delivery for an extended period of time of at least three days and up to seven days or longer, and to eliminate or suppress the high initial release rate of a drug subject to a first order release profile.

Those skilled in the art can readily determine the rate of delivery of drugs from the multiple polymer adhesive system in order to select suitable combinations of polymers and drug for a particular application. Various techniques can be used to determine the rate of delivery of the drug from the polymer. Illustratively, the rate of delivery can be determined by measuring the transfer of drug from one chamber to another through cadaver skin over time, and calculating, from the obtained data, the drug delivery or flux rate.

The compositions of this, invention may further be provided with various thickeners, fillers and other additives known for use with transdermal drug delivery systems. Where the composition tends to absorb water, for example, when lecithin is used as a co-solvent, hydrophilic substances are especially useful. One type of hydrophilic substance which has been successfully employed is clay. The addition of clay has been found to improve adhesiveness in transdermal formulations without reducing the rate of drug delivery. Suitable clays include kaolinites such as baolinite, anauxite, dickite and nacrite, montmorillonites such as montinorillonite, bentonite, berdellite and montronite, illites/muscovites such as illite and glauconite, chlorites, polygorshites such as attapulgite, halloysite, metabolloysite, allophane and aluminum silicate clays.

In a device aspect of the invention, the pressure-sensitive adhesive composition can be used as an adhesive portion of any transdermal drug delivery system (e.g., a reservoir device) or it can comprise an adhesive monolithic. Of course, the principles of the invention would still apply to embodiments where the transdermal drug delivery composition is not a pressure-sensitive adhesive and comprises a drug reservoir.

The configuration of the transdermal delivery system of the present invention can be in any shape or size as is necessary or desirable. Illustratively, a single dosage unit may have a surface area in the range of 1 to 200 cm$^2$. Preferred sizes are from 5 to 60 cm$^2$.

In a method aspect of the invention, a plurality of polymers are blended (but not chemically reacted or cross-linked) to result in a pressure-sensitive adhesive composition which controls delivery of an incorporated drug through the skin or mucosa. The term "blending," of course, incorporates choosing the appropriate polymeric components, and the proportions thereof, to achieve the desired effect.

The present invention is illustrated by the following examples, without limiting the scope of the invention.

EXAMPLES

In the Examples, the effect of variations in the occlusiveness of the backing layer are determined, indicating the flux rate as a function of backing moisture vapor transmission rate. While the Examples are directed to formulations using clonidine, it should be understood that similar drug modulation can be achieved with other active agents, and through the use of other polymers and system configurations as discussed.

All drug-loaded carrier compositions contained 7% clonidine by weight and were prepared using a blend of 83% by weight of a non-functional, acrylic-based pressure sensitive adhesive (DuroTak 73-9301) and 10% by weight of a carboxy functional acrylic-based pressure sensitive adhesive (DuroTak 87-2852). The clonidine and the two acrylic pressure sensitive adhesives were blended together. The composition was coated onto a fluoropolymer release liner and dried for in a 76° C. oven to produce a pressure-sensitive adhesive carrier composition.

Determination of drug flux of the described formulations was conducted on a modified Franz Diffusion cell through a disc of stratum corneum obtained from human cadaver skin. The transdermal system formulations were die-cut to punched, mounted on the disc, and placed on the cell, which contained an isotonic saline solution. The cells were stored at 32° C. for the duration of each flux study while having the solution stirred at a constant rate of approximately 300 rpm.

Example 1

In Example 1, a backing layer comprising polyester and ethylene vinyl acetate was used. The backing layer is commercially available from 3M, as ScotchPak 9732. The backing layer had a moisture vapor transmission rate of 15.5 g/m$^2$/24 hours. The maxtix blend which included 7% by weight clonidine, 83% by weight of a non-functional, acrylic-based pressure sensitive adhesive (DuroTak 73-9301) and 10% by weight of a carboxy functional acrylic-based pressure sensitive adhesive (DuroTak 87-2852) was formed over the backing layer. The matrix was identical to that used in Examples 1 and 3. As can be seen in Table 3, the flux of the transdermal delivery device was 1.69 μg/cm²/hr.

Example 2

In Example 2, a backing layer comprising polyurethane and ethylene vinyl alcohol commercially available from J.P. Stevens Co. of East Hampton, Mass. was used. The backing layer had a moisture vapor transmission rate of 100 g/m²/24 hours. The maxtix blend which included 7% by weight clonidine, 83% by weight of a non-functional, acrylic-based pressure sensitive adhesive (DuroTak 73-9301) and 10% by weight of a carboxy functional acrylic-based pressure sensitive adhesive (DuroTak 87-2852) was formed over the backing layer. The matrix was identical to that used in Examples 1 and 3. As can be seen in Table 3, the flux of the transdermal delivery device was 0.93 μg/cm²/hr.

Example 3

In Example 3, a polyurethane backing layer commercially available from J.P. Stevens Co. of East Hampton, Mass. was used. The backing layer had a moisture vapor transmission rate of 1500 g/m²/24 hours. The maxtix blend included 7% by weight clonidine, 83% by weight of a non-functional, acrylic-based pressure sensitive adhesive (DuroTak 73-9301) and 10% by weight of a carboxy functional acrylic-based pressure sensitive adhesive (DuroTak 87-2852) was formed over the backing layer and was identical to that used in Examples 1 and 2. As can be seen in Table 3, the flux of the transdermal delivery device was 0.32 μg/cm²/hr.

TABLE 3

| | Backing Material | MVTR (g/m²/24 hrs) | Flux (μg/cm2/hr) |
|---|---|---|---|
| Example 1 | PET/EVA | 15.5 | 1.69 |
| Example 2 | PU/EVOH | 100 | 0.93 |
| Example 3 | PU | 1500 | 0.32 |

Figure 2:
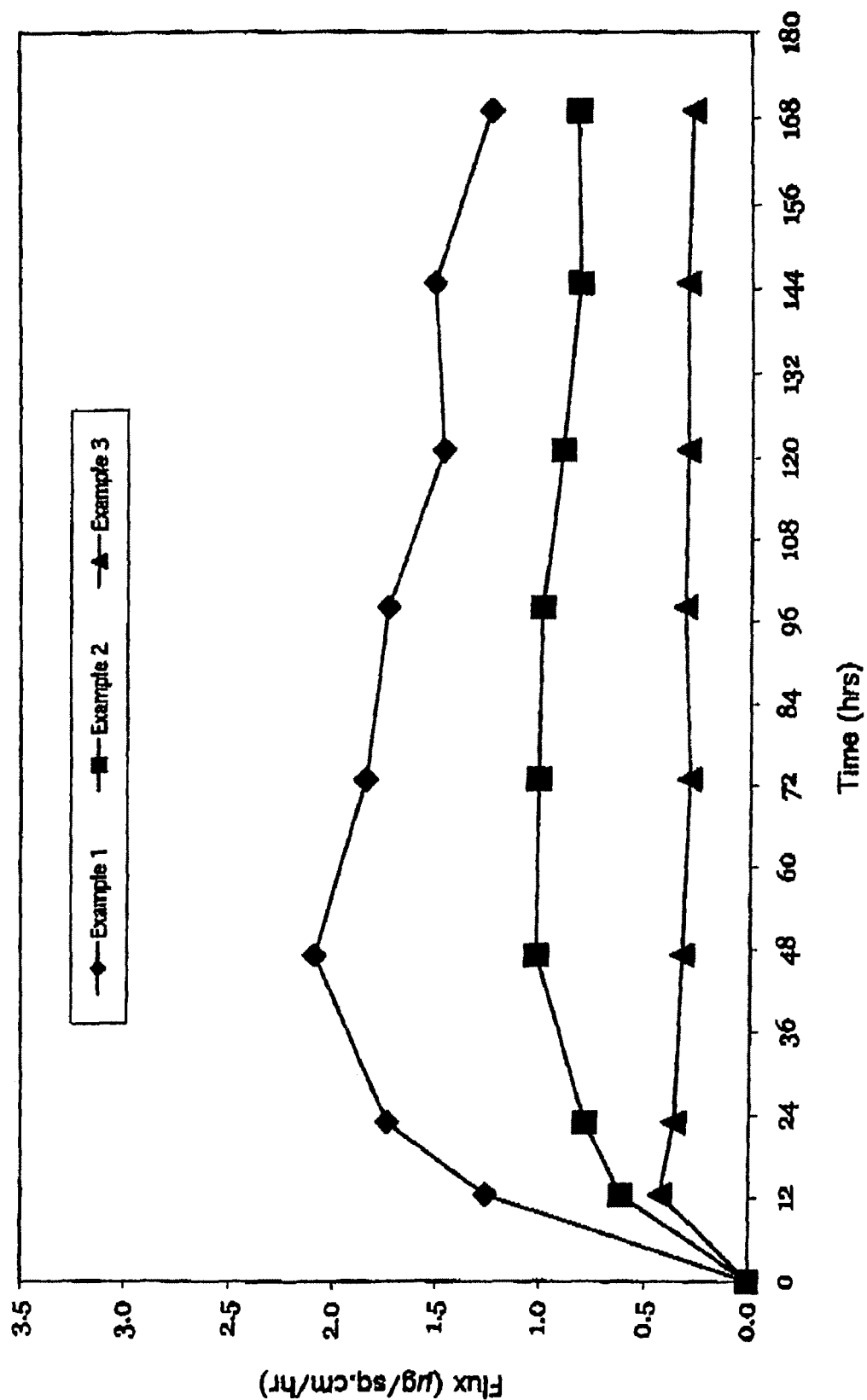
FIG. 2 is a graphic representation of the effects on drug delivery of clonidine in a transdermal delivery device with varying backing layers.

The results from Examples 1 to 3 are set forth graphically in FIG. 2. As illustrated in the forgoing Examples and in FIG. 2, backing layers having a low water vapor transmission rates increase the flux of clonidine. As such, varying the moisture vapor transmission rate of the backing layer can be utilized to control permeation rates of transdermal systems.

The above description and example are only illustrative of preferred embodiments which achieve the objects, features, and advantages of the present invention, and it is not intended that the present invention be limited thereto.

What is claimed is:

1. A transdermal drug delivery system for amphetamine comprising:
   (a) a pressure sensitive adhesive carrier layer comprising
      (i) an acrylic polymer and (ii) a therapeutically effective amount of amphetamine; and
   (b) a backing layer adjacent the carrier layer comprised of polymeric layers consisting of a polyester layer and a polyurethane layer.

2. The transdermal drug delivery system of claim 1, wherein the pressure sensitive adhesive carrier layer comprises a blend of a non-functional acrylic polymer and an acrylic polymer comprising functional groups.

3. The transdermal drug delivery system of claim 2, wherein the acrylic polymer comprising functional groups comprises amide groups.

4. The transdermal drug delivery system according to claim 1, wherein the amphetamine is selected from the group consisting of d-amphetamine, l-amphetamine, d,l-amphetamine, and mixtures thereof.

5. The transdermal drug delivery system according to claim 1, comprising from about 0.5% to about 15% by weight of amphetamine, based on the weight of the carrier layer.

6. The transdermal drug delivery system according to claim 1, comprising about 15% by weight of amphetamine, based on the weight of the carrier layer.

7. The transdermal drug delivery system according to claim 1, wherein the backing layer has a thickness of from about 0.2 mm to about 3 mm.

8. The transdermal drug delivery system according to claim 1, wherein said backing layer has a moisture vapor transmission rate of from 10 to about 100 g/m²/24 hrs.

9. The transdermal drug delivery system of claim 1, further comprising a release liner adjacent a surface of the carrier layer opposite the backing layer.

10. A transdermal drug delivery system for topical application of amphetamine comprising:
    (a) a pressure sensitive adhesive carrier layer consisting essentially of a blend of a non-functional acrylic polymer and an acrylic polymer comprising amide functional groups and a therapeutically effective amount of amphetamine; and
    (b) a backing layer adjacent the carrier layer comprised of polymeric layers consisting of a polyester layer and a polyurethane layer.

11. The transdermal drug delivery system of claim 10, further comprising a release liner adjacent a surface of the carrier layer opposite the backing layer.

12. A transdermal drug delivery system for topical application of amphetamine comprising:
    (a) a pressure sensitive adhesive carrier layer consisting of a blend of a non-functional acrylic polymer and an acrylic polymer comprising amide functional groups and a therapeutically effective amount of amphetamine; and
    (b) a backing layer adjacent the carrier layer comprised of polymeric layers consisting of a polyester layer and a polyurethane layer.

13. The transdermal drug delivery system of claim 12, further comprising a release liner adjacent a surface of the carrier layer opposite the backing layer.

14. A method for transdermally delivering amphetamine to a subject in need thereof comprising topically administering the transdermal drug delivery device according to claim 1 to said subject.

15. A method of producing the transdermal drug delivery system according to claim 13, comprising:
    (a) thoroughly and uniformly mixing a non-functional acrylic polymer and an acrylic polymer comprising amide functional groups and a therapeutically effective amount of amphetamine in an appropriate volatile solvent system;
    (b) casting said carrier layer onto a backing film comprised of polymeric layers consisting of a polyester layer and a polyurethane layer and exposing the cast carrier layer to elevated temperatures to remove volatile solvents; and
    (c) applying a release liner to the surface of the carrier layer opposite the backing layer to form the transdermal drug delivery composition.

* * * * *